(12) United States Patent
Herfert et al.

(10) Patent No.: US 7,662,460 B2
(45) Date of Patent: Feb. 16, 2010

(54) PLASTICIZED SUPERABSORBENT POLYMER SHEETS AND USE THEREOF IN HYGIENIC ARTICLES

(75) Inventors: Norbert Herfert, Charlotte, NC (US); Michael A. Mitchell, Waxhaw, NC (US); Friedrich Engelhardt, Frankfurt (DE)

(73) Assignee: BASF Aktiengesellschaft

( * ) Notice: Subject to any disclaimer, the term of this patent is extended or adjusted under 35 U.S.C. 154(b) by 469 days.

(21) Appl. No.: 10/511,193

(22) PCT Filed: Apr. 29, 2003

(86) PCT No.: PCT/EP03/04437

§ 371 (c)(1),
(2), (4) Date: Oct. 12, 2004

(87) PCT Pub. No.: WO03/092757

PCT Pub. Date: Nov. 13, 2003

(65) Prior Publication Data

US 2005/0153123 A1    Jul. 14, 2005

Related U.S. Application Data

(60) Provisional application No. 60/376,961, filed on May 1, 2002.

(51) Int. Cl.
*B32B 3/00* (2006.01)
*A61F 13/15* (2006.01)
*A61F 13/20* (2006.01)

(52) U.S. Cl. .................. 428/156; 604/358; 604/383; 604/370; 604/372; 604/367; 604/368; 428/172

(58) Field of Classification Search ............... 428/156, 428/167, 172; 604/317, 358, 385.23, 380, 604/383, 378, 379, 370, 372, 367, 368
See application file for complete search history.

(56) References Cited

U.S. PATENT DOCUMENTS

| | | | |
|---|---|---|---|
| 3,908,659 A | * | 9/1975 | Wehrmeyer et al. ......... 604/374 |
| 4,076,673 A | | 2/1978 | Burkholder, Jr. |
| 4,861,539 A | | 8/1989 | Allen et al. |
| 5,324,561 A | | 6/1994 | Rezai et al. |
| 5,372,766 A | | 12/1994 | Roe |
| 5,451,353 A | | 9/1995 | Rezai et al. |
| 5,599,335 A | | 2/1997 | Goldman et al. |
| 5,607,550 A | | 3/1997 | Akers |
| 5,614,269 A | | 3/1997 | Hoskins et al. |
| 5,669,894 A | | 9/1997 | Goldman et al. |

(Continued)

FOREIGN PATENT DOCUMENTS

| | | |
|---|---|---|
| EP | 0 690 077 | 6/1995 |
| WO | WO 00/69383 | 11/2000 |

*Primary Examiner*—David R Sample
*Assistant Examiner*—Catherine Simone
(74) *Attorney, Agent, or Firm*—Marshall, Gerstein & Borun LLP

(57) ABSTRACT

A flexible absorbent sheet material containing an acidic water-absorbing resin, a basic water-absorbing resin, and a plasticizer, and its method of manufacture, are disclosed. The sheets contain about 60% to 100% by weight of the acidic and basic water-absorbent resin and plasticizer. The absorbent sheets have unexpected flexibility and structural integrity, while exhibiting exceptional water absorption and retention properties.

24 Claims, 5 Drawing Sheets

U.S. PATENT DOCUMENTS

| | | | |
|---|---|---|---|
| 5,728,085 A * | 3/1998 | Widlund et al. | 604/378 |
| 5,756,159 A | 5/1998 | Hoskins et al. | |
| 5,858,535 A | 1/1999 | Wang et al. | |
| 5,859,074 A | 1/1999 | Rezai et al. | |
| 5,962,578 A * | 10/1999 | Beihoffer et al. | 524/521 |
| 5,980,996 A | 11/1999 | Terry et al. | |
| 5,997,690 A | 12/1999 | Woodrum | |
| 6,011,196 A * | 1/2000 | Wang et al. | 604/368 |
| 6,033,769 A | 3/2000 | Brueggemann et al. | |
| 6,051,317 A * | 4/2000 | Brueggemann et al. | 428/378 |
| 6,072,101 A * | 6/2000 | Beihoffer et al. | 604/372 |
| 6,310,268 B1 | 10/2001 | Rangachariet et al. | |
| 6,323,388 B1 * | 11/2001 | Melius et al. | 604/368 |
| 6,458,877 B1 * | 10/2002 | Ahmed et al. | 524/275 |
| 7,195,810 B1 * | 3/2007 | Schmidt et al. | 428/156 |
| 2002/0007166 A1 | 1/2002 | Mitchell at al. | |

* cited by examiner

PLASTICIZED SUPERABSORBENT POLYMER SHEETS AND USE THEREOF IN HYGIENIC ARTICLES

CROSS-REFERENCE TO RELATED APPLICATIONS

This is the U.S. national phase application of International Application No. PCT/EP03/04437, filed Apr. 29, 2003, which claims the benefit of U.S. provisional patent application Ser. No. 60/376,961, filed May 1, 2002.

FIELD OF THE INVENTION

The present invention is directed to an absorbent sheet material comprising about 60% to 100%, by weight, superabsorbent polymer and plasticizer, its method of manufacture, and to absorbent articles comprising the absorbent sheet material. The absorbent sheet comprises at least one unneutralized acidic water-absorbing resin, at least one unneutralized basic water-absorbing resin, and a plasticizer component. The absorbent sheet material has excellent flexibility and structural integrity for facile manufacture of absorbent articles. The absorbent sheet materials, and articles containing the sheets, exhibit a rapid uptake of large amounts of aqueous media and an excellent retention of the absorbed media.

BACKGROUND OF THE INVENTION AND PRIOR ART

Water-absorbing resins are widely used in sanitary goods, hygienic goods, wiping cloths, water-retaining agents, dehydrating agents, sludge coagulants, disposable towels and bath mats, disposable door mats, thickening agents, disposable litter mats for pets, condensation-preventing agents, and release control agents for various chemicals. Water-absorbing resins are available in a variety of chemical forms, including substituted and unsubstituted natural and synthetic polymers, such as hydrolysis products of starch acrylonitrile graft polymers, carboxymethylcellulose, crosslinked polyacrylates, sulfonated polystyrenes, hydrolyzed polyacrylamides, polyvinyl alcohols, polyethylene oxides, polyvinylpyrrolidones, and polyacrylonitriles.

Such water-absorbing resins are termed "superabsorbent polymers," or SAPs, and typically are lightly crosslinked hydrophilic polymers. SAPs generally are discussed in Goldman et al. U.S. Pat. Nos. 5,669,894 and 5,559,335, each incorporated herein by reference. SAPs can differ in their chemical identity, but all SAPs are capable of absorbing and retaining amounts of aqueous fluids equivalent to many times their own weight, even under moderate pressure. For example, SAPs can absorb one hundred times their own weight, or more, of distilled water. The ability to absorb aqueous fluids under a confining pressure is an important requirement for an SAP used in a hygienic article, such as a diaper.

As used here and hereafter, the term "SAP particles" refers to superabsorbent polymer particles in the dry state, i.e., particles containing from no water up to an amount of water less than the weight of the particles. The terms "SAP gel" or "SAP hydrogel" refer to a superabsorbent polymer in the hydrated state, i.e., particles that have absorbed at least their weight in water, and typically several times their weight in water.

The development of highly absorbent, SAP-containing articles for use as disposable diapers, adult incontinence pads and briefs, and catamenial products, such as sanitary napkins, is the subject of substantial commercial interest. A highly desired feature of such absorbent articles is thinness. For example, thin diapers are less bulky to wear, fit better under clothing, and are less noticeable. Article packaging also is more compact, which makes the diapers easier for the consumer to carry and store. Packaging compactness also results in reduced distribution costs for the manufacturer and distributor, including less required shelf space per diaper unit.

A variety of parameters effect the ability of an SAP particle and an absorbent core to rapidly absorb a large amount of an aqueous fluid, and then retain the absorbed fluid under various stresses. Optimization of these parameters allows a reduction in amounts of cellulosic fiber, or fluff, present in a diaper core, which in turn reduces the overall bulk of the diaper. SAP particles and cores, therefore, are designed in an attempt to optimize absorption capacity, absorption rate, acquisition time, gel strength, and permeability, and decrease core thickness.

The present invention is directed to the surprising and unexpected finding that an absorbent sheet material prepared from an acidic water-absorbing resin, a basic water-absorbing resin, and plasticizer, after thermal pressing, provides a flexible sheet of excellent structural integrity. The sheet exhibits excellent fluid absorption and retention properties, and allows the elimination or reduction of the amount of fluff in the absorbent sheet material.

Absorbent article cores typically contain a relatively low amount (e.g., less than about 50% by weight) of SAP particles for several reasons. First, SAPs employed in present-day absorbent articles lack an absorption rate that allows the SAP particles to quickly absorb body fluids, especially in "gush" situations. This necessitates the inclusion of fibers, typically wood pulp fibers, admixed with an SAP in the absorptive core of the article as temporary reservoirs to hold the discharged fluids until absorbed by the hydrogel-forming absorbent polymer.

In order to manufacture a sheet material for a diaper core substantially, or completely, free of cellulosic fiber, a continuous zone of SAP particles is required. However, because of the nature of SAP particles, it has been impossible to combine features such as high absorption capacity and high gel strength in an SAP because improving one feature adversely affects the other.

In particular, SAPs typically exhibit gel blocking. "Gel blocking" occurs when SAP particles are wetted, and the SAP particles, swell to retard fluid transmission to other regions of the absorbent structure. Wetting of these other regions of the absorbent member takes place via a slow diffusion process. Gel blocking can be a particularly acute problem if the SAP particles do not have adequate gel strength and deform or spread under stress once the particles swell with absorbed fluid. In practical terms, the acquisition of fluids by the absorbent article is much slower than the rate at which a fluid is discharged, especially in a gush situation. Leakage from and/or deformation of the absorbent article can take place well before the SAP particles in the absorbent article are fully saturated or before the fluid can diffuse, or wick, through the "blocking" particles into the remainder of the absorbent core.

The gel blocking phenomena has necessitated the use of a fibrous matrix to disperse the SAP particles, and separate the SAP particles from one another. The fibrous matrix also provides a capillary structure that allows fluid to reach SAP located in regions of the core remote from the initial fluid discharge point. However, dispersing a relatively low amount of the SAP in a fibrous matrix to minimize or avoid gel blocking reduces the total fluid storage capacity of absorbent cores. Overall, using lower amounts of an SAP limits the advantage of the SAP, i.e., an ability to absorb and retain large quantities of body fluids per given volume.

For absorbent sheet materials containing a relatively high amount of SAP particles, other SAP properties also are important. It has been found that the openness, or porosity, of the hydrogel layer formed when the SAP swells in the presence of body fluids helps determine the ability of an SAP to acquire and transport a fluid, especially when the SAP is present in high amounts in the absorbent core. Porosity refers to the fractional volume of a particle that is not occupied by solid material. For a hydrogel layer formed entirely from an SAP, porosity is the fractional volume of the layer that is not occupied by hydrogel. For an absorbent structure containing the hydrogel, as well as other components, porosity is the fractional volume (also referred to as void volume) that is not occupied by the hydrogel or other solid components (e.g., cellulosic fibers).

U.S. Pat. Nos. 4,076,673 and 4,861,539 disclose an absorbent article containing a superabsorbent film prepared by extruding a solution of a linear absorbent polymer and subsequently crosslinking the polymer. The resulting SAP film can absorb significant quantities of liquids, but has limited liquid transport properties because the film is essentially nonporous, i.e., lacks internal capillary channels. Such an SAP film, therefore, is especially prone to gel blocking. Furthermore, because the crosslinking reaction between the hydroxy groups of the crosslinking agent, e.g., glycerol, and the carboxy groups of the SAP is relatively slow, i.e., glycerol-treated linear polymers typically are cured at 200° C. for 50 minutes, relatively brittle sheets of bonded absorbent particles result. These friable sheets are difficult to handle, especially in the manufacture of the ultimately desired absorbent articles.

Absorbent sheets of the present invention overcome problems associated with diaper cores containing absorbent sheets having a high percentage of SAP. A sheet material of the present invention is flexible and has high structural integrity for ease of sheet manufacture, handling, and the manufacture of diaper cores. A present sheet material is prepared from a mixture of an unneutralized acidic water-absorbing resin, an unneutralized basic water-absorbing resin, and a plasticizer, which, after thermal pressing, provides an improved absorbent sheet material for use in an absorbent article. The acidic and basic water-absorbing resin can be present as a physical blend, i.e., a mixed bed of acidic resin particles and basic resin particles, or the acidic and basic resins can be present in a single multicomponent superabsorbent resin particle.

In addition to providing an absorbent sheet material having excellent fluid absorption and retention properties, the sheet material is sufficiently flexible and has sufficient structural integrity to be continuously manufactured and formed into rolls for economical transport and storage. Rolls of the sheet material facilitate the manufacture of absorbent articles, especially absorbent articles that are free of fluff.

Other investigators attempted to manufacture a continuous roll of a sheet material that contains a high percentage of a particulate SAP, such as sodium polyacrylate. Examples of fibrous substrates impregnated with superabsorbent polymer are found in U.S. Pat. Nos. 5,614,269; 5,980,996; and 5,756,159, wherein a fibrous substrate is impregnated with the monomer, which subsequently is polymerized in situ by UV light to form an SAP in contact with the fibrous substrate.

Other patents, including U.S. Pat. Nos. 5,607,550 and 5,997,690, disclose the continuous manufacture of a fibrous substrate containing about 50% to 60% SAP particles by the wet, papermaking process. In accordance with the wet process, the fibers and superabsorbent particles are mixed with copious quantities of water, or other liquid medium capable of swelling the SAP particles, and deposited onto a water-pervious support member, generally a Fourdinier wire, where a majority of the water is removed leaving a wet mass of fibers and SAP particles. The wet mat is transferred from the pervious support member and consolidated under heat and pressure to form a fibrous substrate having the SAP particles distributed throughout.

Difficult problems encountered in the continuous manufacture of an absorbent sheet material containing a relatively high percentage of SAP particles include achieving structural integrity of the sheet both during and after manufacture, and overcoming a significant loss (shakeout) of superabsorbent particles from the sheet. Another significant problem has been insufficient flexibility of the absorbent sheet, wherein a "hard," brittle sheet difficult is to handle without breakage and impossible to form into a roll for storage, shipment, and the facile manufacture of an absorbent core.

In accordance with the present invention, it has been found, unexpectedly, that a continuous sheet material formed from unneutralized acidic water-absorbing resin and unneutralized basic water-absorbing resin particles (i.e., each 0% to about 50% neutralized), and a plasticizer, can be manufactured to provide a water-absorbent sheet material containing about 60% to 100% by weight of the acidic and basic water-absorbent resins and plasticizer. The SAPs used to form a sheet material of the present invention can be separate acidic resin particles and basic resin particles, or can be multicomponent particles containing both the acidic and basic resins in a single particle. The sheet materials have new and unexpected flexibility and structural integrity during and after manufacture, in addition to excellent fluid absorption and retention properties.

SUMMARY OF THE INVENTION

In brief, the present invention is directed to an absorbent sheet material manufactured from a mixture containing an unneutralized acidic water-absorbing resin, an unneutralized basic water-absorbing resin, and a plasticizer. The absorbent sheet material can be manufactured, preferably continuously, to provide a sheet containing about 60% to 100% by weight of the acidic and basic water-absorbing resins and the plasticizer. The unneutralized acidic and basic water-absorbing resins can be present in the sheet material of the present invention as separate acidic and basic resin particles, or as multicomponent particles containing both the acidic and basic resins in a single particle.

The present absorbent sheet materials have new and unexpected flexibility and structural integrity, with little or no shakeout, or loss, of SAP particles from the sheet during or after manufacture. The sheets are sufficiently flexible to be formed into rolls, and to be incorporated into absorbent cores of any desired shape.

The sheet materials of the present invention especially exhibit exceptional water absorption and retention properties with respect to electrolyte-containing aqueous liquids, and thereby overcome the salt poisoning effect. The salt poisoning effect and how it is overcome by an SAP containing an unneutralized acidic water-absorbing resin and an unneutralized basic water-absorbing resin is discussed in U.S. Pat. Nos. 6,072,101; 6,159,591; 6,222,091; 6,235,965; and 6,342,298, each incorporated herein by reference. In addition, the absorbent sheet materials have an ability to absorb large amounts of aqueous media quickly, demonstrate good fluid permeability and conductivity into and through the sheet material or an absorbent core containing the sheet material, and resist gel blocking. The sheet material also has a high gel strength, such that a hydrogel formed from the sheet material, upon hydration, resists deformation under an applied stress or pressure.

The present sheet materials are useful in numerous practical applications, and especially in absorbent cores of an absorbent article. In accordance, with an important feature of the present invention, the flexibility, structural integrity, and absorption and retention properties of the absorbent sheet, including absorption kinetics and gel strength, allow the production of absorbent cores free of cellulosic fibers.

Therefore, the present invention is directed to an absorbent sheet material prepared from (a) an SAP component comprising at least one unneutralized acidic water-absorbing resin, such as a poly(acrylic acid), and at least one unneutralized basic water-absorbing resin, such as a poly(vinyl-amine) or a polyethyleneimine, and (b) a plasticizer component, such as propylene glycol or glycerol. The SAP component can be (a) multicomponent superabsorbent particles, as disclosed in U.S. Pat. Nos. 6,072,101; 6,159,591; 6,222,091; 6,235,965; and 6,342,298, each incorporated herein by reference, (b) a mixture of (i) multicomponent superabsorbent particles and (ii) particles of an unneutralized acidic water-absorbing resin, an unneutralized basic water-absorbing resin, or both, or (c) a mixture of (i) particles of an unneutralized acid water-absorbing resin and (ii) particles of an unneutralized basic water-absorbing resin. The absorbent sheet is prepared by admixing the SAP component particles, the plasticizer component, and any optional ingredients, then subjecting the resulting mixture to sufficient heat and pressure for a sufficient time to form a flexible sheet. At high pressures no additional heating is necessary.

The heat and pressure of the thermal pressing or pressing at high pressure is sufficient to form a sheet having sufficient structural integrity to be handled and used in the manufacture of absorbent articles. The heat and pressure or the pressure alone, and time of treatment, is sufficiently mild such that essentially no surface crosslinking reaction occurs between the functional groups of the acidic and basic resin and any functional group present on the plasticizer, i.e., the plasticizer is not consumed in the thermal pressing step.

The absorbent sheet material, therefore, has sufficient flexibility and structural integrity to be continuously manufactured and formed into a roll. The combination of absorption properties and physical properties allow the manufacture of fluffless diaper cores from the present absorbent sheets.

Accordingly, one aspect of the present invention is to provide an absorbent sheet material comprising SAP particles that have a high absorption rate, have good permeability and gel strength, overcome the salt poisoning effect, and demonstrate an improved ability to absorb and retain electrolyte-containing liquids, such as saline, blood, urine, and menses.

Another aspect of the present invention is to provide an absorbent sheet material comprising (i) an SAP component comprising multicomponent SAP particles containing at least one discrete microdomain of at least one acidic water-absorbing resin in contact with, or in close proximity to, at least one microdomain of at least one basic water-absorbing resin, and (ii) a plasticizer component.

Yet another aspect of the present invention is to provide an absorbent sheet material wherein the SAP component comprises a mixture containing (i) multi-component SAP particles and (ii) particles of a second water-absorbing resin selected from the group consisting of an unneutralized acidic water-absorbing resin, an unneutralized basic water-absorbing resin, and a mixture thereof. The SAP component of this embodiment contains about 10% to about 90%, by weight, multicomponent SAP particles and about 10% to about 90%, by weight, particles of the second water-absorbing resin.

Another aspect of the present invention is to provide an absorbent sheet material wherein the SAP material comprises a mixture containing (i) particles of an unneutralized acidic water-absorbing resin and (ii) particles of an unneutralized basic water-absorbing resin. The mixture contains about 10% to about 90%, by weight, acidic resin particles and about 10% to about 90%, by weight, basic resin particles.

Still another aspect of the present invention is to provide absorbent articles, such as diapers and catamenial devices, having an absorbent core comprising one or more absorbent sheets of the present invention. The absorbent article comprises a core, wherein the core contains greater than 50%, and up to 100%, by weight, of the absorbent sheets.

These and other aspects and advantages of the present invention will become apparent from the following detailed description of the preferred embodiments.

DETAILED DESCRIPTION OF THE PREFERRED EMBODIMENTS

Figure 1:
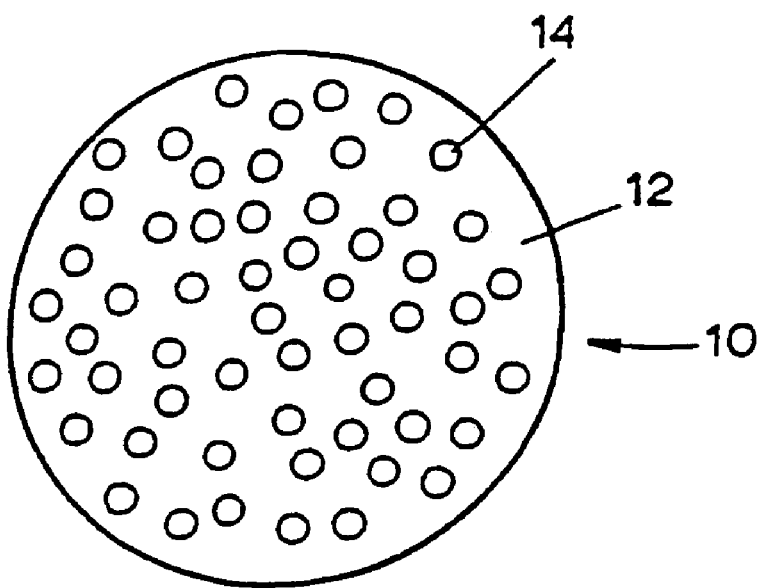
FIG. 1 is a schematic diagram of a water-absorbing particle containing microdomains of a first resin dispersed in a continuous phase of a second resin.

In accordance with the present invention, an absorbent sheet material is manufactured, preferably continuously, from a mixture containing (a) an SAP component and (b) a plasticizer component, and any desired optional ingredients. The SAP component comprises an unneutralized acidic water-absorbing resin and an unneutralized basic water-absorbing resin. The acidic and basic resins can be incorporated into the sheet material as separate particles of each resin, or as multicomponent SAP particles, wherein each particle contains at least one microdomain of the acidic water-absorbing resin and at least one microdomain of the basic water-absorbing resin. The plasticizer component is a material capable of plasticizing one or both of the acidic and basic water-absorbing resins. Preferably, the plasticizer component is nonvolatile under the thermal pressing conditions used to manufacture the absorbent sheet.

The present absorbent sheets exhibit unexpected flexibility and structural integrity for sheets containing about 60% to 100%, by weight, SAP and plasticizer components, and 0% to about 40%, by weight, optional nonabsorbent fibers or fillers, conventional SAPs, and other optional ingredients. The absorbent sheets also exhibit little to no shakeout of SAP particles from the sheet. Accordingly, the absorbent sheets can be incorporated into a core of an absorbent article that is free of fluff. The absorbent sheet materials are useful, for example, as diaper cores, in catamenial devices and other hygienic devices, absorptive pads, wipes, and other absorptive articles for personal or industrial use.

SAP Component

The present invention is directed to an absorbent sheet having an SAP component comprising an unneutralized acidic water-absorbing resin and an unneutralized basic water-absorbing resin. As used herein, the term "unneutralized" is defined as a water-absorbing resin neutralized 0% to 50%. In accordance with an important feature of the present invention, the SAP particles of the SAP component have a particle size of about 10 to about 810 µm, and a median particle size of less than about 400 µm.

In one embodiment, the SAP component comprises multicomponent SAP particles containing at least one microdomain of an acidic water-absorbing resin in close proximity to, and preferably in contact with, at least one microdomain of a basic water-absorbing resin. Each particle contains one or more microdomains of an acidic resin and one or more microdomains of a basic resin. The microdomains can be distributed nonhomogeneously or homogeneously throughout each particle. The multi-component SAP particles have a particle size distribution of about 10 to about 810 µm and have a mass median particle size less than about 400 µm.

Each multicomponent SAP particle contains at least one acidic water-absorbing resin and at least one basic water-absorbing resin. In one embodiment, the SAP particles consist essentially of acidic resins and basic resins, and contain microdomains of the acidic and/or basic resins. In another embodiment, microdomains of the acidic and basic resins are dispersed in an absorbent matrix resin as defined in U.S. Pat. No. 6,159,591.

The multicomponent SAP particles are not limited to a particular structure or shape. However, it is important that substantially each multicomponent SAP particle contains at least one microdomain of an acidic water-absorbing resin and at least one microdomain of a basic water-absorbing resin in close proximity to one another. Improved water absorption and retention, and improved fluid permeability through and between multicomponent SAP particles, are observed as long as the acidic resin microdomain and the basic resin microdomain are in close proximity within the particle. In a preferred embodiment, the microdomains of acidic and basic resin are in contact.

In one embodiment, the multicomponent SAP particles of the present invention can be envisioned as one or more microdomains of an acidic resin dispersed in a continuous phase of a basic resin, or as one or more microdomains of a basic resin dispersed in a continuous acid resin. These idealized multicomponent SAP particles are illustrated in FIG. 1 showing an SAP particle 10 having discrete microdomains 14 of a dispersed resin in a continuous phase of a second resin 12. If microdomains 14 comprise an acidic resin, then continuous phase 12 comprises a basic resin. Conversely, if microdomains 14 comprise a basic resin, then continuous phase 12 is an acidic resin.

Figure 2:
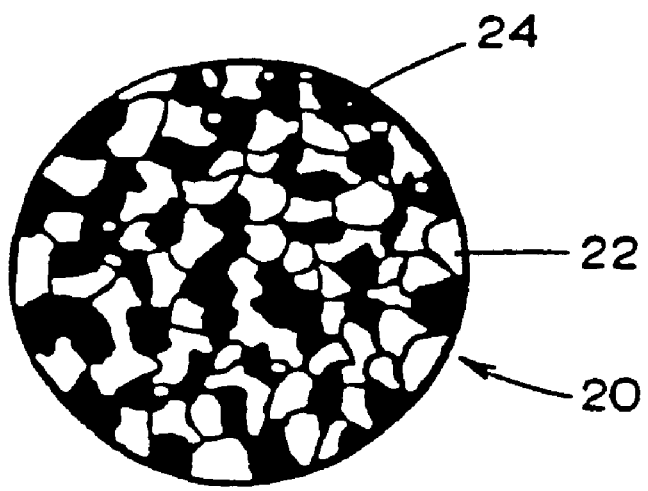
FIG. 2 is a schematic diagram of a water-absorbing particle containing microdomains of a first resin and microdomains of a second resin dispersed throughout the particle.

In another embodiment, the SAP particles are envisioned as microdomains of an acidic resin and microdomains of a basic resin dispersed throughout each particle, without a continuous phase. This embodiment is illustrated in FIG. 2, showing an idealized multicomponent SAP particle 20 having a plurality of microdomains of an acidic resin 22 and a plurality of microdomains of a basic resin 24 dispersed throughout particle 20.

In yet another embodiment, microdomains of the acidic and basic resins are dispersed throughout a continuous phase comprising a matrix resin. This embodiment also is illustrated in FIG. 1 wherein multicomponent SAP particle 10 contains one or more microdomains 14, each an acidic resin or a basic resin, dispersed in a continuous phase 12 of a matrix resin. Additional embodiments of multicomponent SAP particles are disclosed in U.S. Pat. Nos. 6,159,591 and 6,342,298.

The multicomponent SAP particles comprise an acidic resin and a basic resin in a weight ratio of about 90:10 to about 10:90, and preferably about 20:80 to about 80:20. To achieve the full advantage of the present invention, the weight ratio of acidic resin to basic resin in a multicomponent SAP particle is about 30:70 to about 70:30. The acidic and basic resins can be distributed homogeneously or nonhomogeneously throughout the SAP particle.

The multicomponent SAP particles contain at least about 50%, and preferably at least about 70%, by weight of acidic resin plus basic resin. To achieve the full advantage of the present invention, a multicomponent SAP particle contains about 80% to 100% by weight of the acidic resin plus basic resin. Components of the present SAP particles, other than the acidic and basic resin, typically, are matrix resins or other minor optional ingredients.

The multicomponent SAP particles, and particles of other SAP materials, can be in any form, either regular or irregular, such as granules, fibers, beads, powders, or flakes, or any other desired shape. In embodiments wherein the multicomponent SAP is prepared using an extrusion step, the shape of the SAP is determined by the shape of the extrusion die. The shape of the SAP particles also can be determined by other physical operations, such as milling or by the method of preparing the particles, such as agglomeration.

In accordance with an important feature of the present invention, the particles of the SAP component have a particle size distribution of about 10 to about 810 microns (µm), and preferably about 10 to about 600 µm. In more preferred embodiments, the SAP particles have a particle size distribution of about 20 to about 500 µm. To achieve the full advantage of the present invention, the SAP particles have a particle size distribution of about 30 to about 375 µm. The particles of the SAP component also have a mass median particle size of less than about 400 µm, and preferably less than about 350 µm. To achieve the full advantage of the present invention, the SAP particles have a mass median particle size of less than about 300 µm. In preferred embodiments, the SAP particles of the SAP component are in the form of a granule, a bead, or fiber.

For the SAP particles described above, particle size is defined as the dimension determined by sieve size analysis. Thus, for example, a particle that is retained on a U.S.A. Standard Testing Sieve with 250 micron openings (e.g., No. 60 U.S. Series Alternate Sieve Designation) is considered to have a size greater than 250 microns; a particle that passes through a sieve with 250 micron openings and is retained on a sieve with 125 micron openings (e.g., No. 120 U.S. Series Alternate Sieve Designation) is considered to have a particle size between 125 and 250 microns; and a particle that passes through a sieve with 125 micron openings is considered to have a size less than 125 microns.

The mass median particle size of a given sample of SAP is defined as the particle size that divides the sample in half on a mass basis, i.e., one-half of the sample has a particle size greater than the mass median size. A standard particle-size plotting method (wherein the cumulative weight percent of the particle sample retained on or passed through a given sieve size opening is plotted versus sieve size opening on probability paper) typically is used to determine median particle size when the 50% mass value does not correspond to the size opening of a U.S.A. Standard Testing Sieve. Methods for determining the particle size of the SAP particles are further described in U.S. Pat. No. 5,061,259, incorporated by reference.

A microdomain is defined as a volume of an acidic resin or a basic resin that is present in a multicomponent SAP particle. Because each multicomponent SAP particle contains at least one microdomain of an acidic resin, and at least one microdomain of a basic resin, a microdomain has a volume that is less than the volume of the multicomponent SAP particle. A microdomain, therefore, can be as large as about 90% of the volume of a multicomponent SAP particle.

Typically, a microdomain has a diameter of about 100 µm or less. To achieve the full advantage of the present invention, a microdomain has a diameter of about 20 µm or less. The multicomponent SAP particles also contain microdomains that have submicron diameters, e.g., microdomain diameters of less than 1 µm, preferably less than 0.1 µm, to about 0.01 µm.

In another embodiment, the multicomponent SAP particles are in the shape of a fiber, i.e., an elongated, acicular SAP particle. The fiber is in the shape of a cylinder, for example, having a minor dimension (i.e., diameter) and a major dimension (i.e., length). Cylindrical multicomponent SAP fibers have a minor dimension (i.e., diameter of the fiber) less than about 250 µm, and down to about 20 µm. The cylindrical SAP fibers have a relatively short major dimension, for example, about 100 to about 500 µm.

An acidic water-absorbing resin present in a multicomponent SAP particle can be either a strong or a weak acidic water-absorbing resin. The acidic water-absorbing resin can be a single resin, or a mixture of resins. The acidic resin can be a homopolymer or a copolymer. The identity of the acidic water-absorbing resin is not limited as long as the resin is capable of swelling and absorbing at least ten times its weight in water, when in a neutralized form. The acidic resin is present in its acidic, or unneutralized, form, i.e., 50% to 100% of the acidic moieties are present in the free acid form. As illustrated hereafter, although the free acid form of a acidic water-absorbing resin is generally a poor water absorbent, the combination of an acidic resin and a basic resin either in a multicomponent SAP particle or a mixed bed system provides excellent water absorption and retention properties.

The acidic water-absorbing resin typically is a lightly crosslinked acrylic resin, such as lightly crosslinked polyacrylic acid. The lightly crosslinked acidic resin conventionally is prepared by polymerizing an acidic monomer containing an acyl moiety, e.g., acrylic acid, or a moiety capable of providing an acid group, i.e., acrylonitrile, in the presence of a crosslinker, i.e., a polyfunctional organic compound. The acidic resin can contain other copolymerizable units, i.e., other monoethylenically unsaturated comonomers, well known in the art, as long as the polymer is substantially, i.e., at least 10%, and preferably at least 25%, acidic monomer units. To achieve the full advantage of the present invention, the acidic resin contains at least 50%, and more preferably, at least 75%, and up to 100%, acidic monomer units. The other copolymerizable units can, for example, help improve the hydrophilicity of the polymer.

Ethylenically unsaturated carboxylic acid and carboxylic acid anhydride monomers useful in the acidic water-absorbing resin include acrylic acid, methacrylic acid, ethacrylic acid, α-chloroacrylic acid, α-cyanoacrylic acid, β-methylacrylic acid (crotonic acid), α-phenylacrylic acid, β-acryloxypropionic acid, sorbic acid, α-chlorosorbic acid, angelic acid, cinnamic acid, p-chlorocinnamic acid, β-stearylacrylic-acid, itaconic acid, citraconic acid, mesaconic acid, glutaconic acid, aconitic acid, maleic acid, furmaric acid, tricarboxyethylene, and maleic anhydride.

Ethylenically unsaturated sulfonic acid monomers include aliphatic or aromatic vinyl sulfonic acids, such as vinylsulfonic acid, allyl sulfonic acid, vinyl toluene sulfonic acid, styrene sulfonic acid, acrylic and methacrylic sulfonic acids, such as sulfoethyl acrylate, sulfoethyl methacrylate, sulfopropyl acrylate, sulfopropyl methacrylate, 2-hydroxy-3-methacryloxypropyl sulfonic acid, and 2-acrylamide-2-methylpropane sulfonic acid.

As set forth above, polymerization of acidic monomers, and copolymerizable monomers, if present, most commonly is performed by free radical processes in the presence of a polyfunctional organic compound. Crosslinking renders the acidic resins substantially water insoluble, and, in part, serves to determine the absorption capacity of the resins. For use in absorption applications, an acidic resin is lightly crosslinked, i.e., has a crosslinking density of less than about 20%, preferably less than about 10%, and most preferably about 0.01% to about 7%.

A crosslinking agent most preferably is used in an amount of less than about 7 wt %, and typically about 0.1 wt % to about 5 wt %, based on the total weight of monomers. Examples of crosslinking monomers are disclosed in U.S. Pat. No. 6,159,591.

The acidic resin, either strongly acidic or weakly acidic, can be any resin that acts as an SAP in its neutralized form. The acidic resins typically contain a plurality of carboxylic acid, sulfonic acid, phosphonic acid, phosphoric acid, and/or sulfuric acid moieties. Examples of acidic resins include, but are not limited to, polyacrylic acid, hydrolyzed starch-acrylonitrile graft copolymers, starch-acrylic acid graft copolymers, saponified vinyl acetate-acrylic ester copolymers, hydrolyzed acrylonitrile copolymers, hydrolyzed acrylamide copolymers, ethylene-maleic anhydride copolymers, isobutylene-maleic anhydride copolymers, poly(vinylsulfonic acid), poly(vinylphosphonic acid), poly(vinylphosphoric acid), poly(vinyl-sulfuric acid), sulfonated polystyrene, poly (aspartic acid), poly(lactic acid), and mixtures thereof. The preferred acidic resin is a poly-(acrylic acid).

The multicomponent SAPs can contain individual microdomains that: (a) contain a single acidic resin or (b) contain more than one, i.e., a mixture, of acidic resins. The multicomponent SAPs also can contain microdomains wherein, for the acidic component, a portion of the acidic microdomains comprise a first acidic resin or acidic resin mixture, and the remaining portion comprises a second acidic resin or acidic resin mixture.

Analogous to the acidic resin, the basic water-absorbing resin can be a strong or weak basic water-absorbing resins. The basic water-absorbing resin can be a single resin or a mixture of resins. The basic resin can be a homopolymer or a copolymer. The identity of the basic resin is not limited as long as the basic resin is capable of swelling and absorbing at least 10 times its weight in water, when in a charged form. The weak basic resin typically is present in its free base, or unneutralized, form, i.e., 50% to about 100% of the basic moieties, e.g., amino groups, are present in a neutral, uncharged form. The strong basic resins typically are present in the hydroxide (OH) or bicarbonate ($HCO_3$) form.

The basic water-absorbing resin typically is a lightly crosslinked acrylic type resin, such as a poly(vinylamine) or a poly(dialkylaminoalkyl (meth)acrylamide). The basic resin also can be a polymer such as a lightly crosslinked polyethylenimine, a poly(allylamine), a poly(allylguanidine), a poly (dimethyidiallylammonium hydroxide), a quaternized polystyrene derivative, a guanidine-modified polystyrene, a quaternized poly((meth)acrylamide) or ester analog, or a poly (vinylguanidine). The lightly crosslinked basic water-absorbing resin can contain other copolymerizable units and is cross-linked using a polyfunctional organic compound, as set forth above with respect to the acidic water-absorbing resin.

A basic water-absorbing resin used in the multicomponent SAP particles typically contains an amino or a guanidino group. Accordingly, a water-soluble basic resin also can be crosslinked in solution by suspending or dissolving an uncrosslinked basic resin in an aqueous or alcoholic medium, then adding a di- or polyfunctional compound capable of crosslinking the basic resin by reaction with the amino groups of the basic resin. Examples of such crosslinking agents are disclosed in U.S. Pat. No. 6,235,965.

The basic resin, either strongly or weakly basic, therefore, can be any resin that acts as an SAP in its charged form. The basic resin typically contains amino or guanidino moieties. Examples of basic resins include a poly(vinylamine), a polyethylenimine, a poly(vinylguanidine), a poly(allyl-amine), a poly(allylguanidine), or a poly(dialkyl-aminoalkyl (meth) acrylamide) prepared by polymerizing and lightly crosslinking a monomer having the structure

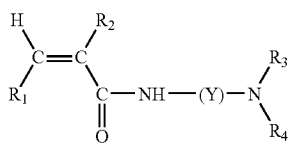

or its ester analog

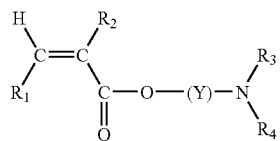

wherein $R_1$ and $R_2$, independently, are selected from the group consisting of hydrogen and methyl, Y is a divalent straight chain or branched organic radical having 1 to 8 carbon atoms, and $R_3$ and $R_4$, independently, are alkyl radicals having 1 to 4 carbon atoms. Preferred basic resins include a poly(vinylamine), polyethylenimine, poly(vinylguan-idine), poly(dimethylaminoethyl acrylamide) (poly-(DAEA)), and poly(dimethylaminopropyl methacryl-amide) (poly (DMAPMA)). Analogous to microdomains of an acidic resin, the multicomponent SAPs can contain microdomains of a single basic resin, microdomains containing a mixture of basic resins, or microdomains of different basic resins.

The multicomponent SAPs can be prepared by various methods. It should be understood that the exact method of preparing a multicomponent SAP is not limited. Any method that provides a particle having at least one microdomain of an acidic resin in contact with or in close proximity to at least one microdomain of a basic resin is suitable. Examples of methods for preparing multicomponent SAPs are disclosed in U.S. Pat. Nos. 6,159,591 and 6,342,298.

The acidic resin, the basic resin, and/or the multicomponent SAP particles optionally can be surface treated and/or annealed, prior to thermal pressing. Surface treatment and/or annealing of SAP particles is known, for example, in U.S. Pat. No. 6,159,591. Nonlimiting examples illustrating multicomponent SAP particles and this method of preparation can be found in U.S. Pat. Nos. 6,159,591 and 6,342,298.

In accordance with an important feature of the present invention, a strong acidic resin can be used with either a strong basic resin or a weak basic resin, or a mixture thereof. A weak acidic resin can be used with a strong basic resin or a weak basic resin, or a mixture thereof. In more preferred embodiments, the weak acidic resin, the weak basic resin, and/or the multicomponent SAP particles are surface crosslinked and/or annealed.

In another embodiment, the SAP component comprises multicomponent SAP particles admixed with particles of a second water-absorbing resin. The second water-absorbing resin can be an unneutralized acidic water-absorbing resin, an unneutralized basic water-absorbing resin, or a mixture thereof. Like the multicomponent SAP particles, the second water-absorbing resin particles have a particle size distribution of about 10 to about 810 µm, and a mass median particle size of less than about 400 µm. The second water-absorbing resin is neutralized 0% to 50%.

An SAP component of this embodiment comprises about 10% to about 90%, and preferably about 25% to about 85%, by weight, multicomponent SAP particles and about 10% to about 90%, and preferably, about 25% to about 85%, by weight, particles of the second water-absorbing resin. More preferably, this embodiment of the SAP component contains about 30% to about 75%, by weight, multicomponent SAP particles. To achieve the full advantage of the present invention, the SAP component contains about 35% to about 75%, by weight, the multicomponent SAP particles. The multicomponent SAP particles and particles of the second water-absorbing resin can be of any shape, e.g., granular, fiber, powder, or platelets.

The second water-absorbing resin can be any of the previously discussed acidic resins used in the preparation of a multicomponent SAP. A preferred acidic water-absorbing resin used as the second resin is unneutralized poly(acrylic acid) (PM), e.g., DN up to 50%. The second water-absorbing resin also can be any of the previously discussed basic resiris used in the preparation of a multicomponent SAP. Preferred basic water-absorbing resins used as the second resin are unneutralized poly(vinylamine) (PVAm) or unneutralized polyethylenimine (PEI). Blends of acidic resins, or blends of basic resins, can be used as the second water-absorbing resin. Blends of an acidic resin and a basic resin also can be used as the second water-absorbing resin. The second water-absorbing resin optionally is surface crosslinked or annealed, prior to the thermal pressing step.

An example of an SAP component of this embodiment is a mixture of multicomponent SAP particles and unneutralized (DN=0) polyacrylic acid (PAA) particles. As used here and throughout the specification PAA(DN=0) refers to 100% unneutralized PAA. The multicomponent SAP particles contain microdomains of PVAm dispersed in PAA(DN=0). The PVAm/PAA weight ratio of the multicomponent SAP particles is 55/45.

Yet another embodiment of the SAP component comprises an admixture of particles of an unneutralized basic water-absorbing resin, like a PVAm, and particles of an unneutralized acidic water-absorbing resin, like PAA, wherein both the acidic and basic water-absorbing resins have a particle size of about 10 to about 810 µm and a median particle size of less than about 400 µm. Both the acidic and basic water-absorbing resin are neutralized 0% to 50%. The acidic and basic water-absorbing resins can be any of the previously discussed acidic and basic resins used in the preparation of a multicomponent SAP, and either or both are optionally surface crosslinked or annealed.

The SAP component of this embodiment comprises about 10% to about 90%, and preferably about 25% to about 85%, by weight, acidic water-absorbing resin particles and about 10% to about 90%, and preferably, about 25% to about 85%, by weight, basic water-absorbing resin particles. More preferably, this embodiment of the SAP component contains about 30% to about 75%, by weight, acidic resin particles. To achieve the full advantage of the present invention, this embodiment of the SAP component contains about 35% to about 75%, by weight, the acidic resin particles.

A preferred acidic water-absorbing resin is PAA (DN=0). Preferred basic water-absorbing resins used are an unneutralized PVAm or an unneutralized PEI. Blends of acidic resins and/or blends of basic resins can be used in the SAP component.

An example of an SAP component of this embodiment is a mixture of unneutralized (DN=0) PAA particles and unneutralized PVAm particles. The PVAm/PAA weight ratio is 45/55 or 30/70.

The superabsorbent component of an absorbent sheet material of the present invention, therefore, can be separate acid and basic resin particles, or multicomponent SAP particles each containing at least one microdomain of an acidic water-absorbing resin and at least one microdomain of a basic water-absorbing resin. Both the acidic and basic water-absorbing resins, whether present as single component particles or as multicomponent particles, are slightly crosslinked polymers that are unneutralized, such that the acidic and basic resins, when wetted, achieve ion exchange between the two resins for particle neutralization.

The superabsorbent component employed in a present absorbent sheet material includes two distinctly different resin species, one acidic and one basic, that are capable of acting as an absorbent material when both are included in the sheet material and contacted by an electrolyte-containing solution. Neither resin in its uncharged form behaves as an SAP by itself when contacted with water. When contacted with an aqueous fluid, like urine, the two uncharged resins are at least partially neutralized to form a superabsorbent material.

Plasticizer Component

An absorbent sheet material of the present invention also comprises a plasticizer component. The plasticizer component is present in the sheet in an amount of about 0.1 to about 200 weight parts per 100 weight parts of SAP component. In preferred embodiments, the sheet material contains about 1 to about 100, and more preferably about 2 to about 50, weight parts of plasticizer component per 100 weight parts of SAP component. To achieve the full advantage of the present invention, the sheet material contains about 3 to about 50, and more preferably about 5 to about 25, weight parts of plasticizer component per 100 weight parts of SAP component. It has been found that if the plasticizer component is present in an amount of greater than 200 weight parts per 100 weight parts of SAP component, then it is difficult to control the thickness of the absorbent sheet, and the sheet may be too thick for efficient use in an absorbent article.

The plasticizer component reduces stiffness, brittleness, and/or rigidity of the sheet, and allows deformation of the absorbent sheet material without substantial cracking, tearing, splitting, breaking, or otherwise fracturing of the sheet material. In addition, the reduction in stiffness, brittleness, and/or rigidity is permanent.

The identity of the plasticizer component is not limited as long as the plasticizer is capable of plasticizing the acidic and/or basic resin of the SAP component. Typically, the plasticizer component affects the basic resin, and plasticizing of the basic resin alone is sufficient to impart excellent flexibility to the absorbent sheet material.

Preferably, the plasticizer component has a sufficiently low volatility at conditions used to thermally press the absorbent sheet to remain in the absorbent sheet after thermal pressing. In preferred embodiments, the plasticizer component contains compounds having a boiling point of about 80° C. or higher, for example, about 80° C. to 250° C.

However, relatively high volatility compounds also can be used in a plasticizer component to facilitate manufacture of a present absorbent sheet material. In this case, at least a portion of the highly volatile compound evaporates during thermal pressing of the sheet material. The highly volatile compound typically is used as a diluent for other compounds present in the plasticizer component to facilitate application of the plasticizer component to particles of the SAP component, and to help ensure a uniform distribution of the plasticizer component on the SAP component. A high volatility compound used in the plasticizer component has a boiling point of at least 20° C. at standard temperature and pressure.

Classes of compounds useful in the plasticizer component include, but are not limited to, alcohols, glycols, triols, polyhydroxy compounds, amine alcohols, amides, sulfoxides, glycol ethers, glycol esters, aprotic solvents, and similar classes of compounds. Alcohols, like methanol and ethanol, typically are highly volatile compounds that evaporate during thermal pressing or storage of the absorbent sheets and used to facilitate sheet manufacture.

Nonlimiting examples of specific compounds useful in the plasticizing component include glycerol; propylene glycol; ethylene glycol; hexylene glycol; 1,3-butylene glycol; diethylene glycol; triethylene glycol; 1,3-propanediol; pentaerythritol; 1,4-butane diol; diacetone alcohol; water; trimethylolpropane; trimethylolethane; neopentyl glycol; cyclohexanedimethanol; isopropylidene bis(p-phenyleneoxypropanol-2); polyethylene glycol (M.W. 500 or less); polypropylene glycol (M.W. 500 or less); polybutylene glycol (M.W. 500 or less); methanol; ethanol; butanol; mono-, di-, and triacetin; the monomethyl, ethyl, butyl, and phenyl ethers of ethylene glycol, diethylene glycol, propylene glycol, dipropylene glycol, and tripropylene glycol, e.g., monomethyl ether of propylene glycol or monoethyl ether of ethylene glycol; dimethylformamide; diethylformamide; N-methylpyrrolidone; dimethyl sulfoxide; triethanolamine; diethanolamine; tetrahydrofuran; ethylene carbonate; isophorone; dioxane; hexamethylphosphoramide; sorbitol; a sorbitan fatty acid ester; aqueous sucrose; and mixtures thereof.

The plasticizer component also can comprise a citrate having a formula:

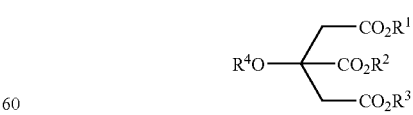

wherein $R^1$, $R^2$, and $R^3$, independently, are $C_{1-4}$alkyl and $R^4$ is selected from the group consisting of hydrogen, $C_{1-4}$alkyl, and $C(O)R^5$, wherein $R^5$ is an alkyl group. Examples of citrates include, but are not limited to, trimethyl citrate, acetyl trimethyl citrate, triethyl citrate, tri-n-butyl citrate, acetyl triethyl citrate, acetyl tri-n-butyl citrate, acetyl tri-n-hexyl citrate, n-butyryl tri-n-hexyl citrate, acetyl tri-n-(hexyl/octyl/decyl) citrate, acetyl tri-n-(octyl/decyl) citrate, and mixtures thereof.

A nonionic surfactant also is useful as a component of the plasticizer component. Useful surfactants have a hydrophobic base, such as a long-chain alkyl group or an alkylated aryl group, and a hydrophilic chain comprising a sufficient number (i.e., 6 to about 20) of ethoxy and/or propoxy moieties. Examples of classes of nonionic surfactants include ethoxylated alkylphenols, ethoxylated and propoxylated fatty ($C_{6-22}$) alcohols, polyethylene glycol ethers of methyl glucose, polyethylene glycol ethers of sorbitol, ethylene oxide-propylene oxide block copolymers, ethoxylated esters of fatty ($C_{6-22}$) acids, condensation products of ethylene oxide with long-chain amines or amides, and mixtures thereof.

Exemplary nonionic surfactants useful in the plasticizer component include, but are not limited to, methyl gluceth-10, PEG-20 ethyl glucose distearate, PEG-20 methyl glucose sesquisterate, $C_{11-15}$pareth-20, ceteth-8, ceteth-12, dodoxynol-12, laureth-15, PEG-20 castor oil, polysorbate 20, steareth-20, polyoxyethylene-10 cetyl ether, polyoxyethylene-10 stearyl ether, polyoxyethylene-20 cetyl ether, polyoxyethylene-10 oleyl ether, polyoxyethylene-20 oleyl ether, an ethoxylated nonylphenol, ethoxylated octylphenol, ethoxylated dodecylphenol, an ethoxylated fatty ($C_{6-22}$) alcohol including 6 to 20 ethylene oxide moieties, polyoxyethylene-20 isohexadecyl ether, polyoxyethylene-23 glycerol laurate, polyoxyethylene-20 glyceryl stearate, polyoxyethylene-20 sorbitan monoesters, polyoxyethylene-15 tridecyl ether, and mixtures thereof.

In an alternative embodiment, the acidic resin and/or basic resin is internally plasticized prior to the thermal pressing step. In internal plasticizing, the acidic or basic resin is reacted with a compound having a moiety capable of reacting with a carboxyl or amino group of the SAP (e.g., a glycidyl group) and a residue capable as acting as a plasticizer compound (i.e., a hydroxyl group). For example, the acidic or basic resin can be internally plasticized by reaction with a monoglycidyl ether of ethylene glycol or a similar compound.

Optional Ingredients

An absorbent sheet material of the present invention also can contain 0% to about 40%, and preferably 0% to about 30%, by weight of optional ingredients, in total. To achieve the full advantage of the present invention, the sheet material contains 0% to about 20%, by weight, of optional ingredients, in total. An individual optional ingredient is envisioned as being present from 0% to about 25%, by weight of the sheet material.

Any optional ingredient known to persons skilled in the art of SAPs can be included in the absorbent sheet material, as long as the optional ingredient does not adversely affect the physical properties of the sheet (e.g., flexibility or structural integrity) or the absorbent properties of the SAP component of the sheet. Examples of optional ingredients, including, but are not limited to, conventional SAPs, nonabsorbent fillers, permeation aids, nonwoven fibers, and similar ingredients.

For example, the absorbent sheet can contain up to about 20% by weight of a conventional SAP, particularly a PAA of DN greater than 50, and typically having a DN=65 to 80. The conventional SAP is neutralized by standard alkalis, such as sodium hydroxide, potassium hydroxide, or triethanolamine. In one embodiment, PAA neutralized with triethanolamine provides a plasticized conventional SAP, which does not adversely affect, and can contribute to, the flexibility of the absorbent sheet.

Other conventional SAPs include neutralized, water-swellable polymers or copolymers containing monomeric units of (meth)acrylic acid, maleic acid, itaconic acid, fumaric acid (meth)acrylamide, (meth)acrylonitrile, hydrolysis products, vinyl acetate and hydrolysis products thereof, vinylpyrrolidone, vinylpyridine, vinylsulfonic acid and esters and amides thereof, and N-alkyl and N,N-dialkyl-substituted esters and/or amides of (meth)acrylic acid, or anhydrides and quaternary ammonium compounds of these monomers. In addition, natural water-swellable polymers useful as a conventional SAP in a present absorbent sheet include, but are not limited to, carboxymethylcellulose, hydroxyethylcellulose, hydroxypropylcellulose, methylcellulose, guar seed meal, xanthans, alginates, starch and derivatives thereof, as well as neutralized graft polymers of these natural polymers and the above-listed monomers.

Examples of conventional SAPs include, but are not limited to, hydrolysis products of starch acrylonitrile graft polymers, carboxymethylcellulose, crosslinked polyacrylates, sulfonated polystyrenes, hydroxyzed polyacrylamides, polyvinyl alcohols, starch-acrylic acid graft copolymers, saponified vinyl acetate-acrylic ester copolymers, hydrolyzed acrylonitrile copolymers, hydrolyzed acrylamide copolymers, ethylenemaleic anhydride copolymers, isobutylene-maleic anhydride copolymers, poly(vinylsulfonic acid), poly(vinylphosphonic acid), poly(vinylphosphoric acid), poly(vinylsulfuric acid), sulfonated polystyrene, poly(aspartic acid), poly(lactic acid), and mixtures thereof. Other lightly crosslinked hydrophilic polymers are disclosed in Goldman et al. U.S. Pat. Nos. 5,669,894 and 5,559,335, each incorporated herein by reference. The preferred acidic resin is a neutralized PAA.

Examples of fillers and permeation aids include, but are not limited to sodium silicate, silica, an absorbent clay (e.g., a bentonite), a kaolin clay, chalk, silica gel, silicic acid, active charcoal, and pigments, such as titanium dioxide.

An optional nonwoven fiber can be, for example, polypropylene, polyethylene, a polyester (like polyethylene terephthalate), viscose, rayon, and mixtures thereof. The types of nonwovens available are carded thermal point bond, resin bond, carded thru-air bond, spunbond, meltblown, spun-meltblown-spun (SMS), hydroentangled (spunlace), drylaid thermobonded. Nonwoven fibers impart additional wet strength to a present absorbent sheet when used in an amount of about 10 to about 100 grams per square meter (gsm) of sheet material. It should be noted that a preferred nonwoven fiber is a rolled material, like the above-described nonwovens, they can also be free fibers commingled with the SAP component.

Suitable fibers can be made from polyvinyl chloride, polyvinyl fluoride, polytetrafluoroethylene, polyvinylidene chloride, polyacrylics such as ORLON®, polyvinyl acetate, polyethylvinyl acetate, nonsoluble or soluble polyvinyl alcohol, polyolefins such as polyethylene (e.g., PULPEX®) and polypropylene, polyamides (e.g., nylon), polyesters (e.g., DACRON® or KODEL®), polyurethanes, polystyrenes, and the like.

Hydrophilic fibers are preferred, and include rayon, polyester fibers, such as polyethylene terephthalate (e.g., DACRON®), hydrophilic nylon (HYDROFIL), and the like. Suitable hydrophilic fibers can also be obtained by hydrophilizing hydrophobic fibers, such as surfactant-treated or silica-treated thermoplastic fibers derived from, for example, polyolefins, such as polyethylene or polypropylene, polyacrylics, polyamides, polystyrenes, polyurethanes, and the like.

Preferred sheet materials of the present invention are "fluffless," i.e., are free of cellulosic fibers or other "fluff" materials. However, if desired, a sheet material of the present invention can contain up to about 25% by weight of a fluff material, as defined herein.

For a sheet material containing a "fluff," the "fluff" comprises a fibrous material. Fibers include naturally occurring fibers (modified or unmodified). Examples of suitable unmodified/modified naturally occurring fibers include cotton, Esparto grass, bagasse, kemp, flax, silk, wool, wood pulp, chemically modified wood pulp, and jute. See WO 98/37149 and U.S. Pat. No. 5,859,074, each incorporated herein by reference, for a complete discussion of "hydrophilic" and "fluff" components for use in an absorbent sheet article.

An absorbent sheet material of the present invention is prepared by admixing the SAP component, plasticizer component, and any optional ingredients, then subjecting the resulting mixture to thermal pressing for a sufficient time at a sufficient temperature and pressure to form an absorbent sheet without any substantial surface crosslinking reaction occurring between the SAP component and plasticizer component. As used herein, the term "essentially no surface crosslinking reaction" is defined to mean that at least 90% of the plasticizer component is present in an absorbent sheet, after thermal pressing, in its free, or unreacted, form, as opposed to a reacted residue form, e.g., as in a surface crosslinked form.

Typically, the SAP component, as particles, first is deposited onto a substrate, like a platen or a plastic sheet, as a thin layer. Then the plasticizer component is sprayed, or otherwise applied (e.g., dripped), onto the surfaces of the SAP component particles, followed by thermal pressing. Alternatively, if the SAP component is internally plasticized, the step of applying the plasticizer component to the SAP component prior to thermal pressing can be omitted.

In accordance with an important feature of the present invention, a sufficient amount of the SAP component is spread on the substrate as a layer to ultimately provide an absorbent sheet material having a thickness of about 0.05 to about 1.5 mm, and preferably about 0.1 to about 1 mm. To achieve the full advantage of the present invention, the absorbent sheet has a thickness of about 0.2 to about 0.5 mm, and most preferably about 0.3 to about 0.4 mm.

More particularly, an absorbent sheet material of the present invention is prepared by thermal pressing the SAP and plasticizer components at a temperature of about 30° C. to about 80° C., and preferably about 35° C. to about 70° C. To achieve the full advantage of the present invention, the SAP-plasticizer component mixture is pressed at about 40° C. to about 60° C.

The thermal pressing is conducted at a pressure of about 100 to about 1000 psi (pounds per square inch), and preferably at about 150 to about 600 psi. To achieve the full advantage of the present invention, the thermal pressing is conducted at 200 to about 400 psi, and more preferably at 250 to about 400 psi. The pressure applied during the thermal pressing step can be greater than 1000 psi because adverse effects are not observed, but no further advantages are observed. For example, there is no further increase in sheet density.

The thermal pressing is conducted for about 10 seconds to about 10 minutes, and preferably about 1 minute to about 8 minutes. To achieve the full advantage of the present invention, thermal pressing is performed for about 2 to about 7 minutes, and most preferably about 3 to about 6 minutes.

In accordance with an important feature of the present invention, and as demonstrated hereafter, a dense absorbent sheet imparts structural integrity and unexpectedly exhibits improved diaper core rewet values and acquisition rates. A sheet material of the present invention therefore has a density of about 0.35 to about 0.9, and preferably about 0.45 to about 0.85 g/cc. To achieve the full advantage of the present invention, an absorbent sheet has a density of about 0.65 to about 0.85 g/cc. As an added advantage, a dense absorbent sheet leads to a thin diaper core.

Under the thermal pressing conditions disclosed above, the plasticizer component does not substantially react with functional groups of the SAP component. Accordingly, the thermal pressing step is different from a surface crosslinking reaction step. An important feature of the present invention is to avoid substantial surface crosslinking during thermal pressing of the SAP component-plasticizer component mixture. This is accomplished by utilized a time, temperature, and pressure that is insufficient to accomplish surface crosslinking.

A sufficient amount of the plasticizer component, in its free, unreacted form, therefore, is present in the absorbent sheet material to impart and maintain flexibility in the sheet. When the plasticizer component is substantially consumed in a surface crosslinking reaction during thermal heating, the flexibility and structural integrity of the absorbent sheet material is adversely affected.

Persons skilled in the art are capable of judiciously selecting the thermal pressing temperature, pressure, and time for the particular SAP component and plasticizer component to avoid substantial surface crosslinking. In particular, persons skilled in the art are aware that various compounds useful as plasticizers of a present absorbent sheet also can be used as surface crosslinking agents of an SAP. Persons skilled in the art also are aware of the conditions needed to affect surface crosslinking, and can design thermal pressing conditions to avoid substantial surface crosslinking of the SAP component by the plasticizer component.

Alternatively, instead of thermal pressing, pressure can also be applied at room temperature without additional heating. Typical temperatures are in the range between 15° C. and 25° C. Typical range for the pressure to be applied is between 300 and 2000 bar, preferably between 500 and 1000 bar. Those pressures can be obtained by state of the art calender machines.

In addition, as discussed more fully hereafter, an absorbent sheet of the present invention can be subjected to an embossing step. The embossing step improves the flexibility of the absorbent sheet, and unexpectedly improves the acquisition rate of the absorbent sheet.

The following examples illustrate the preparation of absorbent sheet materials of the present invention.

EXAMPLE 1

A solution containing 0.3 grams propylene glycol and 0.03 grams deionized water was sprayed onto 3 grams of multicomponent superabsorbent particles. The particles are termed SAF particles, and contain 55% PM (DN=0), and 45% PVAm (100% unneutralized), by weight. The SAF particles had a particle size distribution of about 38 to about 355 μm. The sprayed SAP particles were pressed at 15,000 pounds (about 385 psi) for 5 minutes at 50° C. using a Carver 12 in.×12 in. heated platen. The resulting sheet then was heated at 60° C. for 1 hour. After cooling, the sheet remained flexible and could be cut without fracturing the sheet. Under-these conditions, the multicomponent superabsorbent particles were not surface crosslinked by the propylene glycol.

EXAMPLE 2

Three flexible absorbent sheet materials of the present invention were prepared.

(a) Particles of a multicomponent superabsorbent polymers were distributed as a layer onto a 12 cm by 21 cm polyethylene sheet. The multicomponent superabsorbent polymer contained about 70%, by weight, PAA (DN=0) and about 30%, by weight, PVAm (100% unneutralized), and is termed LAF. The LAF particles had a particle size distribution of about 38 µm to about 355 µm. Propylene glycol (0.3 g) was sprayed onto the LAF particles, then a second polyethylene sheet was positioned over the sprayed LAF particles. The sprayed LAF particles then were pressed between the polyethylene sheets for 5 minutes at 45° C. and 15,000 psi (about 385 psi) using a Carver 12 in.×12 in. heated platen. After thermal pressing, and cooling, the polyethylene sheets were removed to provide a flexible absorbent sheet material having excellent structural integrity.

(b) The procedure of (a) was repeated, except the LAF particles were sprayed with a solution containing 0.03 grams DENACOL EX-810 (ethylene glycol diglycidyl ether) and 0.27 grams propylene glycol. In addition to thermal pressing, the absorbent sheet material also was heated at 60° C. for 1 hour. The resulting flexible absorbent sheet was essentially identical to the sheet of (a).

(c) The procedure of (b) was repeated, except the polyethylene sheets were replaced by a sheet of resin bond polypropylene as an open mat of fibers. Accordingly, the resin bond polypropylene fibers remained in the flexible absorbent sheet material. The resin bond fibers did not adversely affect the flexibility of the sheet, and improved the strength of the sheet and the rewet properties of the sheet.

In the test results set forth below, absorbent sheet materials of the present invention were tested for absorption under no load (AUNL) and absorption under load at 0.28 psi and 0.7 psi (AUL (0.28 psi) and AUL (0.7 psi)). Absorption under load (AUL) is a measure of the ability of an SAP to absorb fluid under an applied pressure. The AUL was determined by the methods, disclosed in U.S. Pat. Nos. 5,149,335 and 6,159,591, incorporated herein by reference.

In addition to an ability to absorb and retain relatively large amounts of a liquid, it also is important for an SAP to exhibit good permeability, and, therefore, rapidly absorb the liquid. Therefore, in addition to absorbent capacity, or gel volume, useful SAP materials also have a high gel strength, i.e., the particles do not deform after absorbing a liquid. In addition, the permeability or flow conductivity of a hydrogel formed when SAP particles swell, or have already swelled, in the presence of a liquid is extremely important property for practical use of the SAP particles. Differences in permeability or flow conductivity of the absorbent polymer can directly impact on the ability of an absorbent article to acquire and distribute body fluids.

Many types of SAP particles exhibit gel blocking. "Gel blocking" occurs when the SAP particles are wetted and swell, which inhibits fluid transmission to the interior of the SAP particles and between absorbent SAP particles. Gel blocking can be a particularly acute problem if the SAP particles lack adequate gel strength, and deform or spread under stress after the SAP particles swell with absorbed fluid.

Accordingly, an SAP sheet material can have a satisfactory AUL value, but will have inadequate permeability or flow conductivity to be useful at high concentrations in absorbent structures. In order to have a high AUL value, it is only necessary that the hydrogel formed from the SAP material has a minimal permeability such that, under a confining pressure of 0.3 psi, gel blocking does not occur to any significant degree. The degree of permeability needed to simply avoid gel blocking is much less than the permeability needed to provide good fluid transport properties. Accordingly, SAP materials that avoid gel blocking and have a satisfactory AUL value can still be greatly deficient in these other fluid handling properties.

An important property of the absorbent sheet materials of the present invention is permeability when swollen with a liquid to form a hydrogel zone or layer, as defined by the gel bed permeability (GBP) of the SAP particles. GBP measures the ability of an SAP to transport saline fluids, such as the ability of the hydrogel layer formed from the swollen SAP to transport body fluids. In particular, gel permeability is a property of a mass of SAP particles as a whole, and is related to particle size distribution, particle shape, the connectedness of the open pores, and compressibility of the swollen gel.

When an SAP is present at high concentrations in an absorbent structure, and then swells to form a hydrogel under usage pressures, the boundaries of the hydrogel come into contact, and interstitial voids in this high SAP concentration region become generally bounded by hydrogel. When this occurs, the permeability or saline flow conductivity properties in this region generally is indicative of the permeability or saline flow conductivity properties of a hydrogel zone formed from the SAP alone. Increasing the permeability of these swollen high concentration regions to levels that approach or exceed conventional acquisition/distribution materials, such as wood pulp fluff, can provide superior fluid handling properties for the absorbent structure, thus decreasing incidents of leakage, especially at high fluid loadings.

Accordingly, it would be highly desirable to provide an absorbent sheet material having a high GBP value without adversely affecting rewet values. This is particularly true if high, localized concentrations of an SAP are to be used effectively in an absorbent article. High GBP values also indicate an ability of the resultant hydrogel to absorb and retain body fluids under normal usage conditions. A method for determining the GBP value of SAP particles is set forth in U.S. Pat. No. 6,376,011, incorporated herein by reference. GBP values disclosed herein were measured by the procedure set forth in U.S. Pat. No. 6,376,011, with the exception that a hydration time of 60 minutes prior to measurement of the flow rate was used.

The absorbent sheet materials of the present invention exhibit an excellent AUL at 0.7 psi. A present absorbent sheet material comprising an SAP component of particle size distribution about 38 to about 355 µm also has a GBP value of about 1000 to about 6000, and preferably about 1500 to about 5000. To achieve the full advantage of the present invention, the GBP value is about 2000 and to about 4000.

As discussed hereafter, tests show that thermal pressing to form an absorbent sheet does not adversely affect the absorption and retention properties of the SAP component of the absorbent sheet. Furthermore, the absorbent sheet material has excellent structural integrity and flexibility, making the sheets useful in numerous practical applications.

In particular, prior superabsorbent sheet materials and cores containing a high loading of SAP were inflexible and brittle. This necessitated including a high percentage of fluff material (e.g., at least 50%), like cellulose or hydrophilic fibers in the sheet, to reduce brittleness and impart flexibility. A present absorbent sheet, or absorbent core, can contain 100% SAP component and plasticizer component (i.e., 0% fluff) and still have sufficient flexibility and structural integrity for practical applications. Accordingly, preferred absorbent sheets, and cores, of the present invention include less than 25%, by weight, preferably less than 20%, and more preferably less than 15% and down to 0% fluff.

Another problem encountered by prior superabsorbent sheet materials is gel blocking. The present absorbent sheet contains sufficient void volume such that after fluid absorption gel blocking is avoided. In addition, during absorption, the small individual SAP particles utilized in a present absorbent sheet increase in size, thereby increasing the void volume between particles. This is attributed to the flexibility of the sheet imparted by the plasticizer component. The present absorbent sheets, therefore, are the first sheets containing a high percentage of SAP to be free of gel blocking, and, accordingly, are excellent for use in absorptive articles of manufacture.

The present absorbent sheet materials, therefore, contain an above-described SAP component that has properties such as high gel strength, interparticle adhesion, and gel bed permeability that lend such SAP components to plasticization and thermal bonding into stable, flexible sheets that are free of gel blocking and that maintain a good degree of fluid wicking. The present absorbent sheets are excellent for forming laminates that are thinner, lighter, and perform better than conventional diaper cores in both acquisition rate and rewet properties.

In accordance with an important feature of the present invention, a hygienic product, or other absorbent article, has a core containing about 60% to 100%, by weight, preferably about 70% to 100%, more preferably about 75% to 100%, and most preferably about 80% to 100%, of the superabsorbent component and plasticizer component of the absorbent sheet materials, i.e., are fluffless cores.

Multicomponent SAP particles and mixed beds of resin particles have been used in diaper cores in high amounts, and exhibit excellent acquisition rates, but the rewet values can be very high. This observation is attributed to the open nature of the core after the first hydration, or insult, which causes a loss of capillary action in the core. The open nature of the core after the first hydration is due to particle/particle and particle/fluff adhesion in the core. As the particles swell, these adhesive forces cause the formation of large voids that are incapable of capillary fluid transport.

The present invention preferably utilizes relatively small particle size SAP particles in the SAP component of the sheet to maintain (a) a void space that avoids gel blocking and (b) a capillary wicking action in low fluff and fluffless cores. The present absorbent sheets, therefore, have an inherent capillary wicking action. Normally, a conventional SAP is used at larger particle sizes (e.g., >400 μm) because the hydrating SAP is subject to gel blocking. However, because ion exchanging SAPs can have excellent gel bed permeabilities (i.e., high GBP) even at very small particle sizes, smaller particle size ranges are preferred in low fluff cores. With a sufficiently small SAP particle size, the wicking action is sufficient to allow a complete elimination of the cellulosic fiber. The small particle size SAP in the absorbent sheet is capable of performing both the wicking and storage functions of a core.

An absorbent core comprising an absorbent sheet of the p-resent invention can range from heavily loaded cores (e.g., 60-95 wt % SAP-plasticizer) to fluffless cores (i.e., 100% SAP-plasticizer). The fluffless cores typically are constructed of alternate layers of (a) a wicking layer, like a tissue, and (b) absorbent sheets. Additionally, a top, or acquisition, layer of conventional superabsorbent polymer optionally can be used to provide faster acquisition rates.

A wicking layer preferably is a cellulose tissue, but also can be any layer of material that provides a liquid wicking action, such as hydrophilic polypropylene fibers, polymeric foams (e.g., HIPE, a conventional superabsorbent, a latex, a resorcinol/formaldehyde polymer, or viscose), and higher basis weight celluosics (e.g., paper towels and heavier tissues).

Although some embodiments exclude a wicking layer, and preferred embodiments exclude an acquisition layer, in some embodiments even greater acquisition rates may be desired, or required, for example, in a gush situation in adult incontnence. Acquisition layers include high loft nonwovens, as disclosed in U.S. Pat. No. 5,382,400, curled cellulose fibers, as disclosed in U.S. Pat. No. 4,822,453, HIPE foams, as disclosed in U.S. Pat. No. 5,260,345, superabsorbent from, as disclosed in U.S. Pat. Nos. 5,338,766 and 6,136,873, and hydrophilic nonwovens, as disclosed in WO 01/56625, all incorporated herein by reference.

Present-day diapers generally consist of a topsheet made from a non-woven material that is in contact with the skin of the wearer, an acquisition layer below (i.e., opposite the skin of wearer) the topsheet, a core that is below the acquisition layer, and a backsheet below the core. This construction is well known in the industry. In a preferred embodiment, the present diaper consists essentially of a topsheet, a core, and a backsheet, i.e., an acquisition layer is not present. As illustrated below, improvements provided by the present absorbent sheet material allow omission of an acquisition layer from a disposable diaper. Such a result is important in the art because an expensive acquisition layer can be omitted, the diaper is lighter and thinner, and absorptive properties are not adversely affected.

A single absorbent sheet of the present invention can be used as the absorbent component of an absorbent core. Preferably, a plurality of the absorbent sheets are used in the absorbent core, more preferably together with a wicking layer (e.g., a tissue layer) between absorbent sheets to provide improved wicking of a fluid between and through the absorbent sheets. In more preferred embodiments, at least one of the absorbent sheets in an absorbent core contains nonwoven fibers to improve wet strength of the absorbent core and assist in wicking.

As discussed hereafter, a preferred core contains two to five layers of the present absorbent sheets. By utilizing a laminate of thin absorbent sheets, as opposed to a single, thicker absorbent sheet, horizontal expansion of the core is decreased, and vertical expansion is promoted. This feature provides a good fluid transport through the core, provides a better fitting diaper after an initial insult, and avoids leaking when the diaper is subsequently rewet by a second and additional insult. In more preferred embodiments, the core contains a laminate of two or more absorbent sheets wherein a wicking layer is positioned between each absorbent sheet layer, and on top and at the bottom of the laminate.

An absorbent sheet of the present invention, or a laminate comprising sheets of the present invention, is present in an absorbent core to provide a desired basis weight (i.e., weight of SAP in the core) of about 50 to about 800 gsm (grams/square meter), and preferably about 150 to about 600 gsm. To achieve the full advantage of the present invention, the basis weight is about 300 to about 550 gsm. The desired basis weight of the core is related to the end use of the core. For example, diapers for newborns have a low basis weight, as opposed to a medium basis weight for toddlers, and a high basis weight for overnight diapers.

Figure 3:
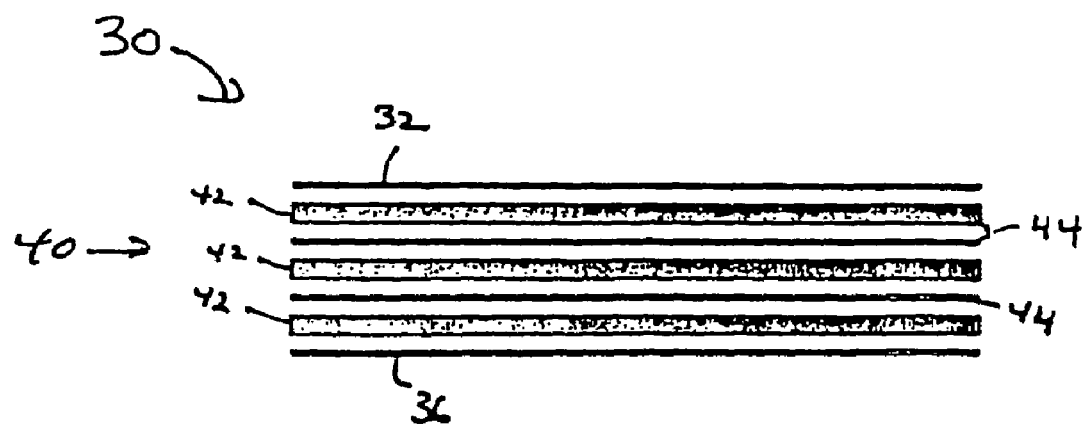
FIGS. 3 and 4 are cross sections of an absorbent article having a core containing 100% by weight absorbent sheets of the present invention as the SAP.

A fluffless core of the present invention is illustrated in FIG. 3. FIG. 3 shows a cross section of an absorbent article 30 having a topsheet 32, a backsheet 36, and an absorbent core indicated by 40 positioned between topsheet 32 and backsheet 36. As shown in FIG. 3, core 40 comprises a plurality of layers 42. Layers 42 comprise an absorbent sheet material of the present invention and are separated from one another by tissue layers 44.

An example of a topsheet 32 is staple length polypropylene fibers having a denier of about 1.5, such as Hercules-type 151 polypropylene marketed by Hercules, Inc., Wilmington, Del. As used herein, the term "staple length fibers" refers to fibers having a length of at least about 15.9 mm (0.62 inches). The backsheet 36 is impervious to liquids, and typically is manufactured from a thin plastic film, although other flexible liquid impervious materials also can be used. The backsheet prevents exudates absorbed and contained in the absorbent core 40 from wetting articles, such as bed sheets and undergarments, that contact the diaper 30.

The fluffless core in FIG. 3 can include an additional layer (not shown) disposed between topsheet 32 and layer 42. This optional additional layer serves as an acquisition/distribution layer and contains a conventional SAP, e.g., PAA (DN=70). A fluffless core illustrated in FIG. 3 can contain one to five, and preferably two to four layers 42, i.e., one to five layers of an absorbent sheet material of the present invention.

In a preferred embodiment, the present diaper core consists essentially of a topsheet, a core, and a backsheet, i.e., an acquisition layer is not present. Improvements provided by present absorbent sheet materials permit an acquisition layer to be omitted from a disposable diaper. Such a result is both new and unexpected in the art in that an expensive acquisition layer can be omitted, the diaper is lighter and thinner, and absorptive properties are not adversely affected.

Cores containing one or more absorbent sheets of the present invention were tested for rewet under a 0.7 psi load, liquid acquisition time, and liquid acquisition rate. The following describes the procedure used to determine the acquisition and rewet under load of a hygienic article, like a diaper. These tests exhibit the rate of absorption and fluid retention of a 0.9%, by weight, saline solution, by a hygienic article over 3 to 5 separate fluid insults while under a load of 0.7 psi.

Apparatus:
100 ml separatory funnel, configured to deliver a flow rate of 7 mil/sec., or equivalent; 3.642 kg circular weight (0.7 psi) 10 cm diameter, with 2.38 cm ID perspex dose tube through the center of weight;
VWR Scientific, 9 cm filter paper or equivalent;
2.5 kg circular weight (0.7 psi)—8 cm diameter;
Digital timer,
Electronic balance (accuracy of a 0.01 gram);
Stopwatch.

Procedure:

1. Preparation
(a) Record the weight (g) of the hygienic article, e.g., diaper, to be tested;
(b) Place hygienic article flat on the bench top, for example, by removing any elastics and/or taping the ends of the article to the bench top;
(c) Place the 3.64 kg circular weight onto the hygienic article with the opening of the perspex dose tube positioned at the insult point (i.e., 5 cm toward the front from the center).

2. Primary Insult and Rewet Test
(a) Measure 100 ml of 0.9% NaCl solution (i.e., 0.9% by weight sodium chloride in deionized or distilled water) into separatory funnel. Dispense the NaCl solution into the perspex tube of the weight at a flow rate of 7 ml/sec and start the timer immediately. Stop the timer when all of the NaCl solution has completely disappeared from the surface of the hygienic article at the base of the perspex tube. Record this time as the primary acquisition time (sec).
(b) After 10 minutes have elapsed, remove the weight and conduct the rewet test procedure:
 (i) Weigh a stack of 10 filter papers, record this value (dry weight).
 (ii) Place the filter papers over the insult point on the hygienic article. Set the timer for 2 minutes. Place the 2.5 kg weight onto the filter papers and start timer immediately.
 (iii) After 2 minutes have elapsed, remove the weight and reweigh the filter papers (wet weight). Subtract the dry weight of the filter papers from the wet weight, this is the rewet value. Record this value as the primary rewet value (g).

3. Secondary Insult and Rewet Test
(a) Place the 3.64 kg weight back onto the hygienic article in the same position as before. Repeat step 2a using 50 ml NaCl solution (recoding the absorption time as the secondary acquisition time) and steps 2b (i)-(iii) using 20 filter paper (recording the rewet values as the secondary rewet).

4. Tertiary, and additional, Insult and Rewet Tests
(a) Place the load back onto the diaper in the same position as before. Repeat step 2a using 50 ml of NaCl solution (recording the absorption time as the tertiary acquisition time) and steps 2b (i)-(iii) using 30 filter paper (recording the rewet value as the tertiary or subsequent rewet).

The following tests were performed to illustrate the new and unexpected benefits provided by an absorbent sheet material of the present invention.

In one test, the amount of plasticizing component was varied, and the effect on various absorption parameters of an absorbent sheet was measured. In particular, the amount of plasticizing component (i.e., propylene glycol) applied to an SAP component (i.e., multicomponent SAP particles containing 55%, by wt., PAA and 45%, by wt., PVAm was varied. The data is summarized in the following table. All data was generated under a 0.7 psi load. In these tests, the absorbent sheet was subjected to a first insult with 100 ml of 0.9% saline, followed by subsequent second, third, and fourth insults with 50 ml of 0.9% saline.

| Wt % PG | 1st (100 ml) | 2nd (50 ml) | 3rd (50 ml) | 4th (50 ml) |
|---|---|---|---|---|
| Average Acquisition Time (sec) | | | | |
| 0 | 197.0 | 82.7 | 60.0 | 68.0 |
| 10 | 124.7 | 81.0 | 61.0 | 51.0 |
| 25 | 69.0 | 15.3 | 24.7 | 44.3 |
| 50 | 82.3 | 20.0 | 16.5 | 34.0 |
| 100 | 85.0 | 14.3 | 16.3 | 19.0 |
| Average Acquisition Rate (ml/sec) | | | | |
| 0 | 0.51 | 0.60 | 0.83 | 0.74 |
| 10 | 0.80 | 0.62 | 0.82 | 0.98 |
| 25 | 1.45 | 3.26 | 2.03 | 1.13 |
| 50 | 1.21 | 2.50 | 3.03 | 1.47 |
| 100 | 1.18 | 3.49 | 3.06 | 2.63 |
| Average Rewet (g/g) | | | | |
| 0 | 0.03 | 0.37 | 2.59 | 5.49 |
| 10 | 0.04 | 0.13 | 2.59 | 5.49 |

-continued

| | | | | |
|---|---|---|---|---|
| 25 | 0.04 | 0.03 | 0.05 | 3.25 |
| 50 | 0.03 | 0.03 | 0.09 | 3.18 |
| 100 | 0.03 | 0.02 | 0.27 | 1.13 |

| Wt. % PG | Core Weight | Core Thickness |
|---|---|---|
| 0 | 11.42 | 0.83 |
| 10 | 12.22 | 0.82 |
| 25 | 13.49 | 0.89 |
| 50 | 15.36 | 1.00 |
| 100 | 19.06 | 1.36 |

The results summarized in the above tables indicate that the optimum amount of plasticizer with respect to acquisition rate (i.e., 1.45 ml/sec in the first (primary) insult) was 25 weight parts propylene glycol per 100 weight parts of the SAP component. This data indicates that the preferred amount of plasticizer component in a present sheet is about 3 to about 50, and more preferably about 5 to about 25, weight parts plasticizer component per 100 weight parts of the SAP component.

The rewet values for the 25, 50, and 100 weight part propylene glycol cores in this test was inconclusive because the permeability of these cores was sufficiently high such that a portion of the primary insult leaked from the edge of the core. SAP utilization of the 0 and 10 weight part propylene glycol cores were excellent, e.g., about 27.6 g/g. For comparison, a commercially available LUVS Leak Guard core has an SAP utilization of about 22.7 g/g. In addition, no appreciable increase in core thickness was observed using 10 to 25 weight parts propylene glycol in the core. SAP utilization is calculated as follows:

Calculation of SAP Utilization:

Rewet measurements were performed until a rewet value of greater three grams was obtained. The rewet measurements were performed in conjunction with the Acquisition Time Under No Load (strike-through) experiment. The total mass added ($g_1$) less the amount in excess of 3 grams given back on the last rewet ($g_2$-3) then is divided by the total mass of SAP in the tested core ($g_3$). Absorptions due to tissue and nonwoven fibers were ignored.

$$SAP\ Utilization = (g_1 - (g_2 - 3))/g_3$$

Sample calculation for sheet 2 above:
Total mass added in grams=total volume added in ml=$g_1$=210
Final rewet in grams=$g_2$=4
Grams of SAP in core=$g_3$=9
SAP utilization=(210−(4−3))/9=23.2 g/g In accordance with an important feature of the present invention, the cores exhibited fast acquisition rates without sacrificing rewet performance. For example, SAP utilization in the various diaper cores shows that a present plasticized, fluffless core having an acquisition/distribution (AD) layer exceeds the performance of commercial cores (i.e., 23.2 g/g versus 19.2 to 22.6 g/g). Furthermore, even in the absence of an AD layer, SAP utilization in a present fluffless core is comparable to commercial products (i.e., 20.0 g/g versus 19.2-22.6 g/g).

The plasticized fluffless cores of the present invention used in the following studies were prepared as follows:

A 21 cm×12 cm rectangular form was placed on a 21 cm×12 cm sheet of tissue overlaid by a 21 cm×12 cm sheet of 15 gsm resin bond nonwoven. Using a salt shaker, three grams of multicomponent superabsorbent polymer particles (50% PVAm/50% PAA, by weight, both DN=0 and particle size range 38-355 μm) were distributed evenly over the tissue and nonwoven fibers. Then, 0.3 grams of propylene glycol (10 weight parts based on the weight of SAP particles) was sprayed onto the SAP particles. The process was repeated in the absence of the nonwoven fiber, and then repeated once more with a sheet of nonwoven fibers. A final layer of tissue was placed on top of the SAP component-plasticizer component mixture. This laminate then was pressed in a Carver Press set at 15,000 pounds pressure (about 385 psi on the 12 cm×12 cm laminate) and 50° C. for 5 minutes. Each sheet was flexible and individual sheets performed as summarized in the following tables.

Figure 4:
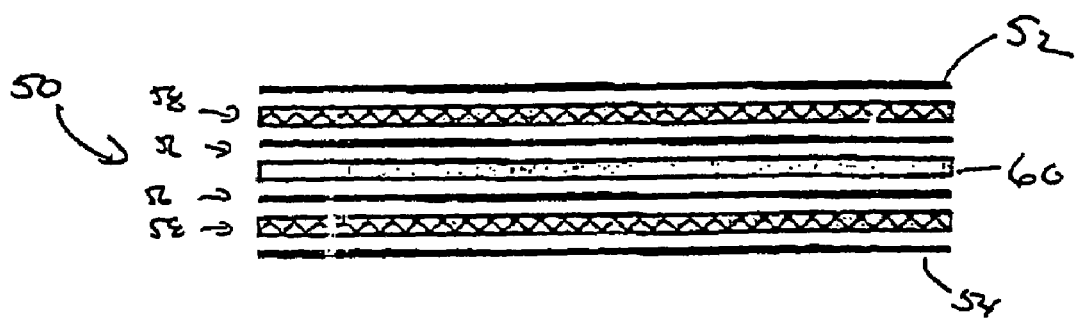

The construction of these plasticized fluffless cores is depicted in FIG. 4 showing a cross section of a three-layer laminated, fluffless absorbent core 50 having a top tissue 52 and a bottom tissue 54, with a plurality of layers positioned between tissues 52 and 54. As shown in FIG. 4, core 50 comprises two layers 58 of sheet material containing an SAP, plasticizer, and a nonwoven fiber. Core 50 also contains a layer 60 of sheet material containing SAP and plasticizer. Layers 58 and 60 are separated from one another by tissue layers 56. The SAP component in layers 58 and 60 have been sprayed with propylene glycol (10 weight parts per 100 weight parts of the SAP component).

| SAP Utilization in a Core | |
|---|---|
| | SAP Utilization (g/g) |
| Huggies UltraTrim | 20.3 |
| Luvs | 21.2 |
| Pampers Baby Dry | 22.6 |
| Pampers Premium | 19.2 |
| Sheet with AD layer | 23.2[1] |
| Sheet without AD layer | 20.0[1] |

[1]Average value for four sheets.

1) Average Value for Four Sheets.

The following table contains acquisition rates for a state-of-the-art commercial diaper and for three-layer laminate cores of the present invention containing 9 grams of multicomponent SAP particles containing 50% PAA and 50% PVAm, by weight, and particle size distribution of 38 to 355 μm, plasticized with 20 weight part propylene glycol per 100 weight parts SAP component, two layers nonwoven fibers, and four layers of tissue made by the method set forth previously. The cores were tested by the above-described acquisition rate procedure, using only a nonwoven topsheet and no AD layer.

| | Acquisition Rate (ml/sec) | | | |
|---|---|---|---|---|
| | 1$^{st}$ | 2nd | 3rd | 4th |
| Huggies Ultra Trim | 0.96 | 0.6 | 0.49 | |
| Press Study[2] | 1.11 | 0.79 | 0.47 | 0.45 |
| Emboss Study[3] | 1.27 | 0.96 | 0.49 | 0.42 |

[2]embodiment wherein the absorbent sheet was pressed to form a flat sheet; and
[3]embodiment wherein the absorbent sheet was embossed.

This data clearly shows that both the primary and secondary acquisition rates of the present core are far superior to a commercial diaper having an AD layer.

Another test was performed to show the improvements in wet strength provided by the presence of a nonwoven fiber in a present absorbent sheet. The tests were performed on cores as illustrated in FIG. 4, and the results are summarized in Table 1.

TABLE 1

Rewet Performance

| No. of Nonwoven Sheets in Core | Placement in Core | Rewet (g/g) | | | |
|---|---|---|---|---|---|
| | | 1st | 2nd | 3rd | 4th |
| 0 | None | 0.10 | 1.2 | 9.3 | 16.4 |
| 1 | Top Layer | 0.07 | 0.46 | 6.5 | 15.6 |
| 1 | Middle Layer | 0.10 | 0.27 | 3.4 | 8.0 |
| 1 | Bottom Layer | 0.07 | 0.13 | 0.77 | 7.0 |
| 2 | Top & Bottom | 0.08 | 0.12 | 0.87 | 3.2 |
| 3 | In each layer | 0.10 | 0.13 | 2.1 | 7.2 |

These results illustrate that a layer of nonwoven fibers in the core improves rewet performance. It is theorized, but not relied upon herein, that nonwoven fibers help minimize formation of ripples and fissures that disrupt fluid flow in the core. Preferably, at least two sheets of nonwoven fibers containing SAP and plasticizer components are present in the core to improve wet strength integrity.

In another test, a core of the present invention was compared to a commercial core, i.e., the core of an UltraTrim diaper, available from Kimberly-Clark, Menasha, Wis. A direct comparison was performed under a 0.7 psi load. The results summarized in Table 3 show that even in the absence of an AD layer, the acquisition rates for a primary (1st) and secondary (2nd) insult are superior to a commercial product recognized in the industry as a premier article. Also, SAP utilization is improved in a present plasticized, fluffless core.

TABLE 3

| Core | SAP Utilization (g/g) | Acquisition Rate (ml/sec) | | | |
|---|---|---|---|---|---|
| | | 1st | 2nd | 3rd | 4th |
| UltraTrim | 24.1 | 0.96 | 0.60 | 0.97 | — |
| 10-20 wt % propylene glycol, 2 layers of nonwoven | 27.8 | 1.00 | 1.19 | 0.63 | 0.67 |

Figure 5:
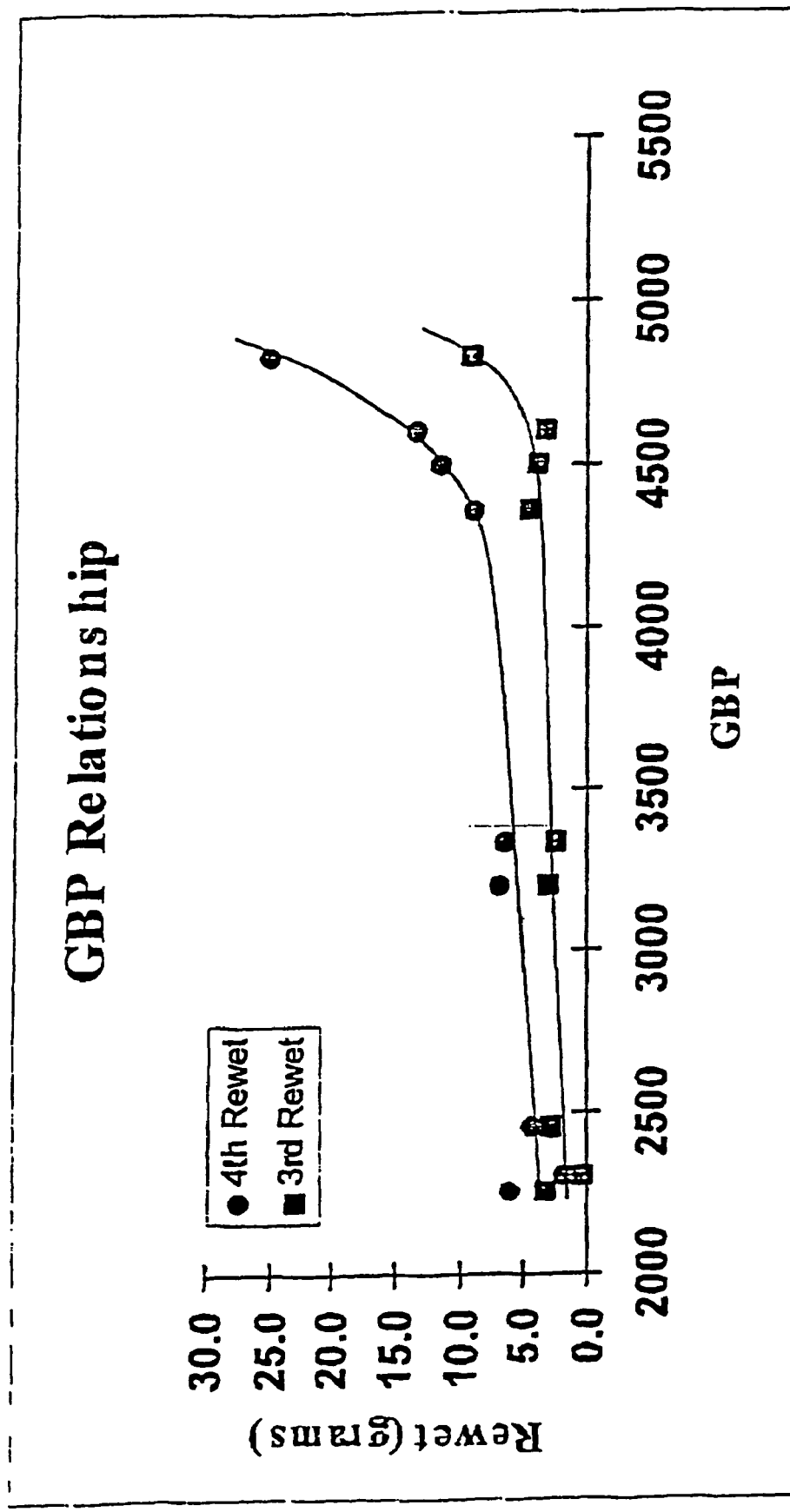
FIGS. 5 and 6 are plots of rewet (g) and acquisition rate (ml/sec) versus gel bed permeability (GBP), respectively, for second, third, and fourth insults to a sheet material of the present invention.
Figure 6:
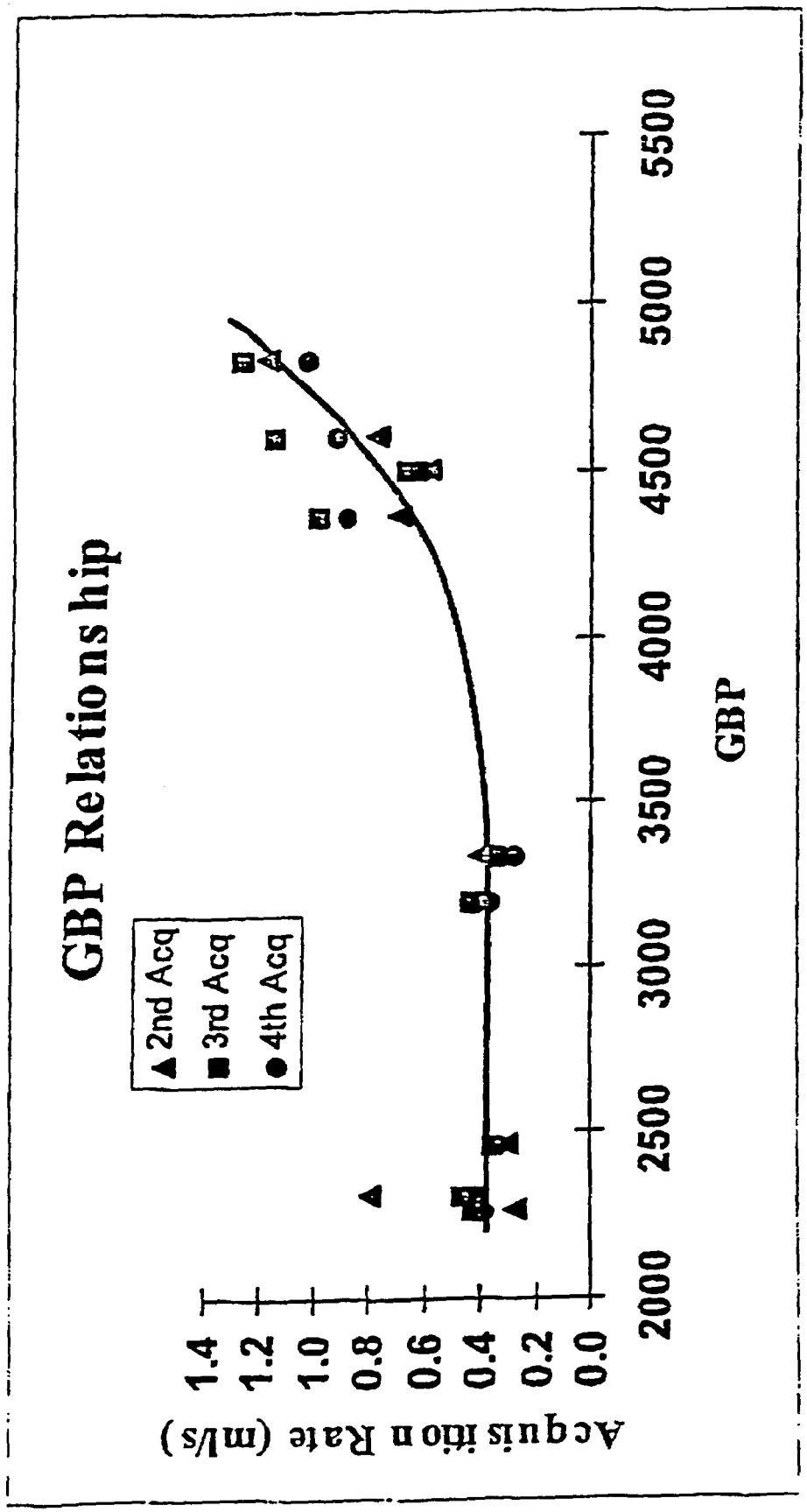

In another test, FIGS. 5 and 6 illustrate the relationship between rewet values (FIG. 5) and acquisition rate (FIG. 6) versus GBP. The GBP testing in FIGS. 5 and 6 was performed on an SAP component having a particle size distribution of about 300 to about 600 μm. These particles then were milled to a particle size distribution of about 38 to about 355 μm SAP particles, which were incorporated into plasticized fluffless cores.

FIGS. 5 and 6 show that acquisition rate increases with GBP, which is desirable, and that rewet values increase above a GBP of 4500, which is undesirable. The phenomena has been attributed to a decrease in wicking ability at very high permeabilities. Accordingly, a present absorbent sheet material utilizing SAP particles of about 38 to about 355 μm in size preferably has a GBP of about 1000 to about 5000, and preferably about 2000 to about 4500.

In general, GBP and rewet values vary with SAP particle size distribution and mass median particle size. Persons skilled in the art are capable of selecting an SAP particle size distribution and mass median particle size-that yield an acceptable balance between GBP and rewet values and provide a useful absorbent sheet material.

In another study, the flexibility of absorbent sheet materials of the present invention were tested. In this test, a single absorbent sheet was prepared by evenly spreading three grams of multicomponent SAP particles containing 50 wt % PVAm/50 wt % PAA on a 12 cm×21 cm sheet of tissue. The weight percentage of propylene glycol sprayed onto the SAP particles was varied. A final tissue was laid over the sprayed SAP particles, and thermal pressing was conducted at 384 psi and 50° C. for 5 minutes. The resulting core was cut into 2.5 cm×15.25 cm strips for testing on a standard Lorentzen & Wettre (A B Lorentzen & Wettre, Kista, Sweden) Resonance Stiffness Tester Model CODE SE 017, as described in the operating instructures.

The results are summarized in the following table:

| Weight Parts Propylene Glycol[3] | Basis Weight (gsm) | Core Density[4] (g/cc) | SAP Component[5] (g/cc) | Stiffness[6] (mNm) |
|---|---|---|---|---|
| 0 | 152 | 0.544 | 0.757 | 6.26 |
| 10 | 164 | 0.589 | 0.842 | 5.59 |
| 25 | 182 | 0.604 | 0.837 | 5.20 |
| 50 | 211 | 0.610 | 0.805 | 4.22 |
| 100 | 271 | 0.583 | 0.665 | 5.15 |

[3] per 100 parts of SAP component;
[4] density of SAP, propylene glycol, and tissue;
[5] density of SAP and propylene glycol only; and
[6] mNm is milliNewtonmeters.

These test results show an immediate reduction in stiffness (i.e., increase in flexibility) upon the addition of propylene glycol. Therefore, an absorbent sheet of the present invention has a stiffness less than about 6.3 mNm, preferably less than about 6, and most preferably less than about 5.5 mNm. An absorbent sheet of the present invention can have a stiffness as low as about 2.5 mNm.

Typically, it is expected that as the basis weight of the core increases, the stiffness of the core also would increase, as in the case of increasing the mass of the present absorbent sheet. This relationship is illustrated in the following table:

| SAP[7] | Basis Weight (gsm) | Stiffness (mNm) |
|---|---|---|
| 0 | 33 | 0.43 |
| 1 | 77 | 2.45 |
| 3 | 164 | 5.59 |
| 5 | 251 | 12.07 |
| 10 | 469 | 28.01 |

[7] 10 parts propylene glycol per 100 parts SAP component (50% PAA (DN = 0) and 50% PVAm 100% unneutralized multicomponent SAP particles).

However, the stiffness data as a function of the weight parts of propylene glycol shows that propylene glycol unexpectedly reduces sheet stiffness in spite of an increased basis weight.

Another set of tests was performed to evaluate the effect of density (g/cc) of the SAP component on core performance. The tested cores had a construction as set forth in FIG. 4. The following table summarizes the relationship between density/compression force and rewet/acquisition rate. In these tests, the following values and calculations were used.

Average tissue mass=0.415 g/12×21 cm sheet

Average tissue thickness=0.09 mm

Average resin bonded nonwoven sheet mass=
 0.363 g/12×21 cm sheet

Average resin bonded nonwoven sheet thickness=
 0.21 mm

Calculation of Core Density (SAP/Plasticizer/Tissues):

Core Density=Mass (12 cm×21 cm×(thickness/10)

Calculation of SAP Density (SAP/Plasticizer):

SAP Density=(Mass-Mass of tissue-Mass of non-woven/(12 cm×21 cm×(thickness-thickness of tissues)/10))

The thickness of the nonwoven was neglected. The cores contained layers of absorbent sheets containing multicomponent SAP particles. (i.e., 50 wt % PAA (DN=0) and 50 wt % PVAm (100% unneutralized), 38-355 μm particle size distribution) and 10 wt. parts propylene glycol per 100 weight parts SAP. All cores had two layers of nonwoven sheets (0.726 grams) and four layers of tissue (1.66 grams, 0.36 mm).

Sample Calculation:

At 26 psi, core mass=12.315 g, and thickness=1.275 mm, then

Core Density=12.315/(12×21×(1.275/10))=0.383 g/cc

SAP Density=(12.315-0.726-1.66)/(12×21×(1.275-0.36)/10))=0.431 g/cc.

density increases over 0 to about 50 weight parts propylene glycol per 100 weight parts SAP component, then decreases, when subjected to a pressure of about 384 psi.

The data in the above table also shows that acquisition rates for the first through fourth insults using 0.9% saline increased as the density of the absorbent sheet material increases. Further, the data in the above table shows that the rewet values for the second through fourth insults dramatically decrease as density of the absorbent sheet increases.

Accordingly, there is a strong relationship between density of the absorbent sheet and acquisition rate, rewet, and stiffness (i.e., flexibility). For example, rewet values drop as the density increases, which is a desired property and attributed to an increased capillary action. An increased capillary action also leads to better core utilization.

Surprisingly, acquisition rates of the cores also increase with density, which is unexpected. It is theorized, but not relied upon, that this unexpected result is a result of increased wicking for better movement of the insult from the insult point, which reduces gel blocking in the insult area.

In summary, the tests show that an absorbent sheet material of the present invention operates exceptionally well when the sheet has a density of about 0.30 to about 0.9 g/cc, preferably about 0.45 to about 0.85 g/cc, and most preferably about 0.65 to about 0.85 g/cc. The density measurements were made by measuring the thickness and mass of a 12 cm×21 cm core, then subtracting the mass and thickness of the tissue layers.

In yet another test, an absorbent sheet of the present invention material was embossed. It is known in the art that embossing, or quilting, increases the flexibility of a sheet material (i.e., a form of mechanical softening). However, it

| Pressure (psi) | Mass (g) | Thickness (mm) | Core Density (g/cc) | Acquisition Time (sec) | | | |
|---|---|---|---|---|---|---|---|
| | | | | 1st (100 ml) | 2nd (50 ml) | 3rd (50 ml) | 4th (50 ml) |
| 26 | 12.315 | 1.275 | 0.383 | 260 | 158 | 183 | 246 |
| 128 | 12.485 | 1.045 | 0.474 | 180 | 112.5 | 177.5 | 198 |
| 258 | 12.345 | 0.925 | 0.530 | 118 | 56.5 | 77.5 | 146.5 |
| 384 | 12.12 | 0.825 | 0.583 | 90 | 63 | 107.5 | 110 |
| 512 | 12.095 | 0.815 | 0.589 | 113.5 | 54 | 84 | 167 |
| 614 | 12.29 | 0.835 | 0.584 | 102.5 | 42 | 65 | 115 |

| Acquisition Rate (ml/sec) | | | | Rewet (grams) | | | | Density |
|---|---|---|---|---|---|---|---|---|
| 1st (100 ml) | 2nd (50 ml) | 3rd (50 ml) | 4th (50 ml) | 1st (100 ml) | 2nd (50 ml) | 3rd (50 ml) | 4th (50 ml) | of SAP |
| 0.38 | 0.32 | 0.27 | 0.20 | 0.085 | 0.585 | 2.935 | 4.59 | 0.431 |
| 0.56 | 0.44 | 0.28 | 0.25 | 0.085 | 0.125 | 1.63 | 3.64 | 0.585 |
| 0.85 | 0.88 | 0.65 | 0.34 | 0.17 | 0.075 | 0.345 | 2.48 | 0.699 |
| 1.11 | 0.79 | 0.47 | 0.45 | 0.075 | 0.09 | 0.28 | 1.11 | 0.831 |
| 0.88 | 0.93 | 0.60 | 0.30 | 0.07 | 0.075 | 0.285 | 3.04 | 0.847 |
| 0.98 | 1.19 | 0.77 | 0.43 | 0.035 | 0.06 | 0.2 | 1.165 | 0.827 |

First, the compression force (i.e., pressure) utilized in a thermal pressing step was related to density (g/cc) of the compressed SAP-plasticizer components. The above table shows that density of the sheets increases over a pressure range of 26 to 512 psi, then begins to decrease.

Figure 7:
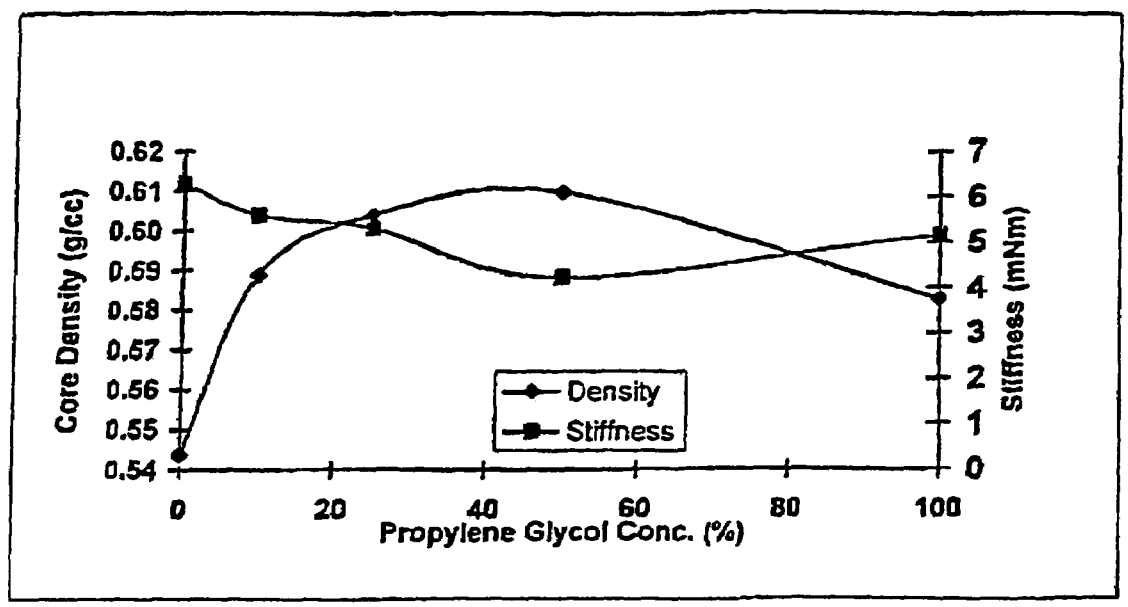
FIG. 7 contains plots of core density (g/cc) and stiffness (mNm) versus propylene glycol concentration.

In addition, the density of an absorbent sheet was compared to the flexibility (i.e., stiffness) of the sheet. The results are summarized in FIG. 7, which shows an inverse relationship between density and stiffness. In particular, FIG. 7 shows the unexpected result of increased flexibility (decreased stiffness) as core density increases. FIG. 7 also illustrates that core also was found that embossing a fluffless diaper core of the present invention increased acquisition rate. Needle punching also can be used to mechanically soften the sheet material of the present invention.

The following tables summarize the results of tests performed on three-layer laminate cores having the construction set forth in FIG. 4, which subsequently were pressed with various mesh screens as an embossing method. The pressure used for the embossing step was 384 psi, using a 12 in.×12 in. Carver Press at 50° C. for 5 minutes.

| Screen Type | Opening Size (mm²) | Wire Diameter (mm) |
|---|---|---|
| Fine | 2 | 0.48 |
| Medium | 16 | 0.80 |
| Coarse | 495 | 3.5 |

| Screen Type | 1st | 2nd | 3rd | 4th |
|---|---|---|---|---|
| | Acquisition Rate (ml/s) | | | |
| Fine | 1.00 | 1.56 | 1.03 | 0.42 |
| Medium | 1.79 | 1.45 | 0.71 | 0.43 |
| Coarse | 3.51 | 0.93 | 0.76 | 0.78 |
| No Embossing | 1.27 | 0.96 | 0.49 | 0.42 |
| | Rewets (grams) | | | |
| Fine | 0.11 | 0.11 | 0.37 | 4.23 |
| Medium | 0.08 | 0.10 | 0.40 | 4.13 |
| Coarse | 0.04 | 0.07 | 1.28 | 7.54 |
| No Embossing | 0.00 | 0.08 | 0.91 | 4.24 |

The cores were tested using a standard nonwoven topsheet, and in the absence of an AD layer. The above tables show that the medium mesh and the coarse mesh provided extremely fast primary, secondary, and tertiary acquisition rates. The fine mesh gives excellent acquisition rates for both the secondary and tertiary insults.

In total, the above tests demonstrate that a diapercore of the present invention, containing one or more of the present absorbent sheets, maintains an essentially constant, or a decreased, acquisition time over four insults. The practical result of this property is a core having an improved ability to prevent leakage in gush situations and in rewet situations, even in the absence of acquisition layers.

The improved results demonstrated by a core of the present invention also permit the thickness of the core to be reduced. Typically, cores contain 50% or more fluff or pulp to achieve rapid liquid absorption while avoiding problems like gel blocking. The present cores, which contain at least one absorbent sheet of the present invention, acquire liquids sufficiently fast to reduce problems, like gel blocking, and, therefore, the amount of fluff or pulp in the core can be reduced or eliminated. A reduction in the amount of the low-density fluff results in a thinner core, and, accordingly, a thinner diaper.

In particular, a present absorbent core has a thickness of about 0.5 to about 2 mm, compared to a thickness of 4 mm for current commercial cores. Further, the diaper is lighter due to the elimination of fluff, i.e., a 10 gram core compared to a currently commercially available core weight of 20 grams.

The plasticized fluffless cores of the present invention typically are more than 50% lighter in mass than a commercial core with the same concentration of SAP. This feature reduces transportation costs and mass of material sent to land fills. In addition, the thickness of these plasticized fluffless cores typically is about 80% less than a commercial diaper core. This feature helps reduce packaging costs and provides an article that is easier to use and wear.

In addition to a thinner diaper core, an acquisition layer can be omitted from the diaper. The acquisition layer in a diaper typically is a nonwoven or fibrous material, typically having a high degree of void space or "loft," that assists in the initial absorption of a liquid. The present cores acquire liquid at a sufficient rate such that diapers free of an acquisition layers are practicable. In particular, an acquisition layer can be omitted because a present diaper core has an acquisition rate of about 1 ml/sec, compared to 0.3 ml/sec for current commercial diapers. Accordingly, simpler and less expensive absorbent articles can be manufactured.

Overall, the sheet materials of the present invention have excellent structural integrity for a nonwoven fabric comprising only an SAP component and a plasticizer component. In particular, the sheet material has sufficient flexibility and structural integrity to be rolled for shipment, storage, and subsequent use.

An absorbent sheet of the present invention is useful in hygienic products, such as diapers, adult incontinence articles, feminine napkins, general purpose wipes and cloths, and in aqueous waste solidification. Other uses include packing containers, drug delivery devices, wound cleaning devices, burn treatment devices, ion exchange column materials, construction materials, agricultural or horticultural materials, such as seed sheets or water-retentive materials, and industrial uses, such as sludge or oil dewatering agents, materials for the prevention of dew formation, desiccants, and humidity control materials.

Many modifications and variations of the invention as hereinbefore set forth can be made without departing from the spirit and scope thereof and, therefore, only such limitations should be imposed as are indicated by the appended claims.

The invention claimed is:

1. A absorbent sheet consisting essentially of:
    (a) a superabsorbent polymer component, as particles, comprising
        (i) at least one unneutralized acidic water-absorbing resin, and
        (ii) at least one unneutralized basic water-absorbing resin, wherein the superabsorbent polymer component is free of interparticle crosslinking; and
    (b) a plasticizing component in an amount of about 0.1 to about 200 parts by weight per 100 weight parts of the superabsorbent polymer component, wherein the sheet contains about 60% to 100%, by weight, of (a) and (b), wherein the sheet material is flexible and has a density of about 0.65 to about 0.85 g/cc, and
    wherein the plasticizing component is present essentially in its unreacted form.

2. The sheet of claim 1 wherein the superabsorbent polymer component comprises discrete particles of the acidic resin and discrete particles of the basic resin.

3. The sheet of claim 1 wherein the superabsorbent polymer component comprises multicomponent superabsorbent polymer particles wherein each particle has at least one microdomain of the acidic resin in contact with, or in close proximity to, at least one microdomain of the basic resin.

4. The sheet of claim 1 wherein the superabsorbent polymer component comprises particles having a particle size distribution of about 10 to about 810 μm.

5. The sheet of claim 1 wherein the superabsorbent polymer component comprises particles having a particle size distribution of about 30 to about 375 μm.

6. The sheet of claim 1 wherein the superabsorbent polymer component comprises particles having a mass median particle size of less than about 400 μm.

7. The sheet of claim 1 wherein the acidic water-absorbing resin is selected from the group consisting of polyacrylic acid, a hydrolyzed starch-acrylonitrile graft copolymer, a starch-acrylic acid graft copolymer, a saponified vinyl acetate-acrylic ester copolymer, a hydrolyzed acrylonitrile polymer, a hydrolyzed acrylamide copolymer, an ethylene-maleic anhydride, copolymer, an isobutylene-maleic anhydride copolymer, a poly(vinylphosphonic acid), a poly(vinylsulfonic acid), a poly(vinylphosphoric acid), a poly(vinylsulfuric acid), a sulfonated polystyrene, a poly(aspartic acid), a poly(lactic acid), and mixtures thereof.

8. The sheet of claim 1 wherein the basic water-absorbing resin is selected from the group consisting of a poly(vinylamine), a poly(dialkylaminoalkyl(meth)acrylamide), a polymer prepared from the ester analog of an N-(dialkylamino (meth)acrylamide), a polyethylenimine, a poly(vinylguanidine), a poly(allylguanidine), a poly(allylamine), a poly(dimethyldialkylammonium hydroxide), a guanidine-modified polystyrene, a quaternized polystyrene, a quaternized poly(meth)acrylamide or ester analog thereof, poly(vinylalcohol-co-vinylamine), and mixtures thereof 9. The sheet of claim 1 wherein the plasticizer component is selected from the group consisting of an alcohol, a glycol, a triol, a polyhydroxy compound, an amine alcohol, an amide, a sulfoxide, a glycol ether, a glycol ester, an aprotic solvent, and mixtures thereof.

10. The sheet of claim 1 wherein the plasticizer component is selected from the group consisting of glycerol; propylene glycol; ethylene glycol; hexylene glycol; 1,3-butylene glycol; diethylene glycol; triethylene glycol; 1,3-propanediol; pentaerythritol; 1,4-butane diol; diacetone alcohol; water; trimethylolpropane; trimethylolethane; neopentyl glycol; cyclohexanedimethanol; isopropylidene bis(p-phenyleneoxypropanol-2); polyethylene glycol (M.W. 500 or less); polypropylene glycol (M.W. 500 or less); polybutylene glycol (M.W. 500 or less); methanol; ethanol; butanol; mono-, di-, and triacetin; the monomethyl, ethyl, butyl, and phenyl ethers of ethylene glycol, diethylene glycol, propylene glycol, dipropylene glycol, and tripropylene glycol, e.g., monomethyl ether of propylene glycol or monoethyl ether of ethylene glycol; dimethylformamide; diethylformamide; N-methylpyrrolidone; dimethyl sulfoxide; triethanolamine; diethanolamine; tetrahydrofuran; ethylene carbonate; isophorone; dioxane; hexamethylphosphoramide; sorbitol; a sorbitan fatty acid ester; aqueous sucrose; a citrate having a formula:

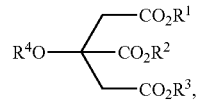

wherein $R^1$, $R^2$, and $R^3$, independently, are $C_{1-4}$alkyl and $R^4$ is selected from the group consisting of hydrogen, $C_{1-4}$alkyl, and $C(O)R^5$, wherein $R^5$ is an alkyl group; an ethoxylated alkylphenol; an and propoxylated fatty ($C_{6-22}$) alcohols; a polyethylene glycol ether of methyl glucose; a polyethylene glycol ether of sorbitol; an ethylene oxide-propylene oxide block copolymer; an ethoxylated ester of fatty ($C_{6-22}$) acid; a condensation product of ethylene oxide with long-chain amine or amide; and mixtures thereof.

11. The sheet material of claim 1 wherein the acidic water-absorbing resin comprises poly(acrylic acid); the basic water-absorbing resin comprises poly(vinylamine), polyethylenimine, or a mixture thereof and the plasticizing agent comprises propylene glycol, glycerol, water, and mixtures thereof.

12. The sheet of claim 1 further comprising up to 40%, by weight in total, of one or more optional ingredient.

13. The sheet of claim 12 wherein the optional ingredient is selected from the group consisting of a conventional superabsorbent polymer, a nonabsorbent filler, a permeation aid, a pigment, and mixtures thereof.

14. The sheet material of claim 1 having a stiffness of less than about 6 mNm.

15. The sheet material claim 1 wherein the sheet is embossed or needle punched.

16. An absorbent article comprising a sheet of claim 1.

17. The article of claim 16 wherein the article is a diaper or a catamenial device.

18. A diaper having a core, said core comprising at least one absorbent sheet of claim 1.

19. The diaper of claim 18 wherein the core comprises two to five of said absorbent sheets.

20. The diaper of claim 19 wherein at least one of adjacent sheets has a wicking layer disposed between the sheets.

21. The diaper of claim 18 further comprising a topsheet in contact with a first surface of the core, and a backsheet in contact with a second surface of the core, said second core surface opposite from said first core surface.

22. The diaper of claim 18 further comprising an acquisition layer disposed between the topsheet and the core.

23. The diaper claim 18 wherein the diaper is free of an acquisition layer.

24. A fluffless absorbent sheet comprising:
(a) a superabsorbent polymer component, as particles, comprising
   (i) at least one unneutralized acidic water-absorbing resin, and
   (ii) at least one unneutralized basic water-absorbing resin, wherein the superabsorbent polymer component is free of interparticle crosslinking;
(b) a plasticizing component in an amount of about 0.1 to about 200 parts by weight per 100 weight parts of the superabsorbent polymer component, wherein the sheet contains about 60% to 100%, by weight, of (a) and (b); and
(c) 0% to 40%, by weight in total, of one or more optional ingredient selected from the group consisting of a conventional superabsorbent polymer, a nonabsorbent filler, a permeation aid, a pigment, and mixtures thereof;
wherein said sheet is free of fibers, is flexible, and has a density of about 0.65 to about 0.85 g/cc and
wherein the plasticizing component is present essentially in its unreacted form.

* * * * *